(12) United States Patent
Oya et al.

(10) Patent No.: US 12,001,531 B2
(45) Date of Patent: Jun. 4, 2024

(54) PATIENT AUTHENTICATION SYSTEM AND PATIENT AUTHENTICATION METHOD

(71) Applicant: Shimadzu Corporation, Kyoto (JP)

(72) Inventors: Kana Oya, Kyoto (JP); Hiroshi Okumura, Kyoto (JP); Junpei Sakaguchi, Kyoto (JP); Tomoharu Okuno, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 757 days.

(21) Appl. No.: 17/071,726

(22) Filed: Oct. 15, 2020

(65) Prior Publication Data
US 2021/0192030 A1   Jun. 24, 2021

(30) Foreign Application Priority Data
Dec. 23, 2019   (JP) .................. 2019-231197

(51) Int. Cl.
*G06F 21/32* (2013.01)
*A61B 6/00* (2024.01)
(Continued)

(52) U.S. Cl.
CPC ............ *G06F 21/32* (2013.01); *A61B 6/5294* (2013.01); *A61B 6/54* (2013.01); *G06V 40/172* (2022.01); *G06V 40/50* (2022.01); *G16H 40/63* (2018.01)

(58) Field of Classification Search
CPC ...... G06F 21/32; G16H 40/63; G06V 40/172; G06V 40/50; A61B 6/5294; A61B 6/54
(Continued)

(56) References Cited

U.S. PATENT DOCUMENTS

2007/0185321 A1* 8/2007 Lee et al.
2008/0212847 A1* 9/2008 Davies .................. G16H 10/40
382/116
(Continued)

FOREIGN PATENT DOCUMENTS

| JP | 2007-185321 A | 7/2007 |
|----|---------------|--------|
| JP | 2014-132 A | 1/2014 |
| WO | WO-2019058537 A1 * | 3/2019 |

OTHER PUBLICATIONS

Iyad Al Khatib,; Security Integration in Medical Device Design: Extension of an Automated Bio-medical Engineering Design Methodology; IEEE:2014; pp. 137-142.*
(Continued)

*Primary Examiner* — Monjur Rahim
(74) *Attorney, Agent, or Firm* — Muir Patent Law, PLLC

(57) ABSTRACT

A patient authentication system is provided with: an authentication unit configured to authenticate a subject based on a reference database, a patient authentication bio-information acquired by a patient bio-information acquisition unit, and patient identification information acquired by a patient identification information acquisition unit, the reference database storing patient reference bio-information acquired in advance as bio-information to be referred to when authenticating the patient and patient reference identification information to be referred to when authenticating the patient in association with each other; and a device control unit configured to perform control of a medical device based on an authentication result which is a result of authentication by the authentication unit.

18 Claims, 9 Drawing Sheets

(51) Int. Cl.
*G06V 40/16* (2022.01)
*G06V 40/50* (2022.01)
*G16H 40/63* (2018.01)

(58) Field of Classification Search
USPC .......................................................... 713/186
See application file for complete search history.

(56) References Cited

U.S. PATENT DOCUMENTS

2013/0336457 A1     12/2013  Arima
2017/0169176 A1*     6/2017  Abiola ................ H04L 63/0428
2019/0042719 A1*     2/2019  Miu .................... H04L 63/0861

OTHER PUBLICATIONS

Notice of Reasons for Refusal dated Feb. 14, 2023 for corresponding Japanese Patent Application No. 2019-231197.
First Office Action, dated Jul. 7, 2023, issued in relation to corresponding Chinese Patent Application No. 202011320022.8, together with a machine English translation thereof.
Second Office Action dispatched on Feb. 29, 2024 for corresponding Chinese Patent Application No. 202011320022.8, and machine translation thereof.

* cited by examiner

PATIENT AUTHENTICATION SYSTEM AND PATIENT AUTHENTICATION METHOD

CROSS-REFERENCE TO RELATED APPLICATIONS

The related application number JP2019-231197, entitled "Patient Authentication System and Patient Authentication Method," filed on Dec. 23, 2019, invented by Kana Oya, Hiroshi Okumura, Junpei Sakaguchi, and Tomoharu Okuno upon which this patent application is based is hereby incorporated by reference in its entirety.

BACKGROUND OF THE INVENTION

Field of the Invention

The present invention relates to a patient authentication system and a patient authentication method.

Description of the Background Art

Conventionally, a radiographic imaging system in which an examination order is acquired via networks is known. Such a radiographic imaging system is disclosed, for example, Japanese Unexamined Patent Application Publication No. 2014-132.

In the radiographic imaging system described in the above-described Japanese Unexamined Patent Application Publication No. 2014-132, when patient information including, e.g., a patient name and a patient ID, and examination information including, e.g., an inspection ID and examination date and time, are input to the search condition input screen, an examination order that matches the input search condition is acquired. Then, X-ray imaging is performed based on the acquired examination order.

Here, when an examination operator, such as, e.g., a doctor and a laboratory technician, performs medical treatment (such as clinical examination) to a patient by using a medical device in a medical institution, such as, e.g., a hospital and a clinic, the name of the examination order and the name of the patient to whom medical treatment is actually performed are checked to prevent a patient error. Although not specifically described in the above-described Japanese Unexamined Patent Application Publication No. 2014-132, in a radiographic imaging system (X-ray imaging apparatus) as described in the above-described Japanese Unexamined Patent Application Publication No. 2014-132, for example, it is considered that the name of the examination order and the name of the patient to whom radiography is performed are checked orally by the examination operator that performs the X-ray imaging (radiography) in order to prevent patient errors.

Generally, when the confirmation result of the patient name (patient authentication result) is correct, the examination operator operates the medical device based on the examination order corresponding to the patient name and the patient ID to perform the examination. When the confirmation result (authentication result) is a patient mismatch, the examination operator performs the task for replacing the patient or changing the examination order. However, there is a problem that when an examination operator performs medical treatment by using a medical device, the task of authenticating a patient and the task of controlling the medical device based on an authentication result are burdensome.

SUMMARY OF THE INVENTION

The present invention has been made to solve the above-mentioned problems, and one object of the present invention is to provide a patient authentication system and a patient authentication method capable of reducing a workload of an examination operator when authenticating a patient and controlling a medical device based on an authentication result.

In order to achieve the above-described object, a patient authentication system according to a first aspect of the present invention includes:
 a patient bio-information acquisition unit configured to acquire patient authentication bio-information which is bio-information for authenticating a patient to whom medical treatment is performed by using a medical device;
 a patient identification information acquisition unit configured to acquire patient identification information for identifying the patient;
 an authentication unit configured to authenticate the patient based on a reference database, the patient authentication bio-information acquired by the patient bio-information acquisition unit, and the patient identification information acquired by the patient identification information acquisition unit, the reference database storing patient reference bio-information acquired in advance as bio-information to be referred to when authenticating the patient and the patient reference identification information to be referred to when authenticating the patient in association with each other; and
 a device control unit configured to perform control of the medical device based on an authentication result which is a result of authentication by the authentication unit.

A patient authentication method according to a second aspect of the present invention includes:
 a step of acquiring patient authentication bio-information which is authentication bio-information of a patient to whom medical treatment is performed by using a medical device;
 a step of acquiring patient identification information for identifying the patient;
 a step of authenticating the patient based on a reference database in which patient reference bio-information acquired in advance as bio-information to be referred to when performing the authentication of the patient and patient reference identification information to be referred to when performing the authentication of the patient are stored in association with each other, the acquired patient authentication bio-information, and the acquired patient identification information; and
 a step of controlling the medical device based on an authentication result which is a result of the authentication.

In the above-described patient authentication system according to the first aspect of the present invention and the above-described patient authentication method according to the second aspect of the present invention, the patient authentication is performed based on the reference database in which patient reference bio-information acquired in advance as bio-information to be referred to when authenticating a patient and patient reference identification information to be referred to when authenticating the patient are stored in association with each other, the patient authentication bio-information acquired by the patient bio-information acquisition unit, and the patient identification information acquired by the patient identification information acquisition unit. With this, the authentication (confirmation) of the patient to whom medical treatment is performed can be automatically performed without performing the confirmation (collation) of the patient by the examination operator based on the identification information, such as, e.g., a patient name and a patient ID. In the present invention, the control of the medical device is performed based on the authentication result which is an authentication result of the authentication unit. As a result, the control of the medical device can be automatically performed as a preparation for performing a medical practice such as a clinical examination based on the authentication result. Consequently, it is possible to reduce the workload of the examination operator at the time of authenticating the patient and controlling the medical device based on the authentication result.

DESCRIPTION OF THE PREFERRED EMBODIMENT

Hereinafter, embodiments in which the present invention is embodied will be described with reference to the attached drawings.

First Embodiment (Configuration of Patient Authentication System)

Referring to FIG. 1 to FIG. 7, a patient authentication system 100 according to a first embodiment will be described.

The patient authentication system 100 in this embodiment is configured to authenticate a patient P by using a face image of the patient P to whom medical treatment (such as, e.g., a clinical examination and radiography) is performed by using a medical device (radiographic imaging device 2). That is, the patient authentication system 100 is configured to authenticate the patient P by using a patient authentication face image A1 which is a face image of the patient P captured in an examination room E where a clinical examination is performed and a patient reference face image A2 which is a face image of the patient P captured in advance.

Note that the patient authentication face image A1 is an example of the "patient authentication bio-information" and the "patient authentication image" recited in claims. Further note that the patient reference face image A2 is an example of the "patient reference bio-information" and the "patient reference image" recited in claims.

Figure 1:
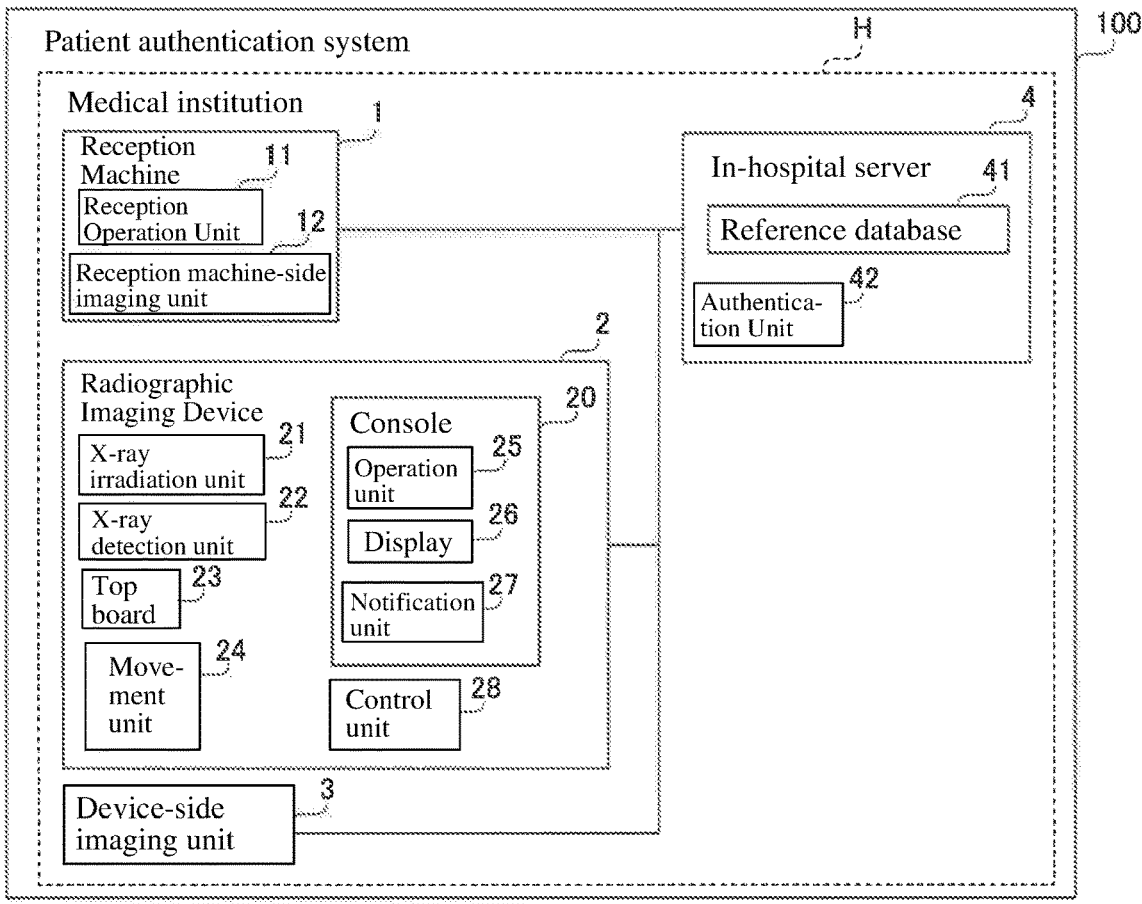
FIG. 1 is a block diagram for explaining the configuration of a patient authentication system according to a first embodiment.

As shown in FIG. 1, the patient authentication system 100 in this embodiment is provided with a reception machine 1, a radiographic imaging device 2, a device-side imaging unit 3, and an in-hospital server 4. The reception machine 1, the radiographic imaging device 2, the device-side imaging unit 3, and the in-hospital server 4 are installed in a medical institution H (for example, a hospital, a clinic, etc.) where the patient P has a clinical examination. The reception machine 1, the radiographic imaging device 2, the device-side imaging unit 3, and the in-hospital server 4 are connected by a network, such as, e.g., a LAN (Local Area Network) and are configured to be able to transmit and receive data to and from each other.

Note that the radiographic imaging device 2 is an example of the "medical device" recited in claims. Further note that the device-side imaging unit 3 is an example of the "patient bio-information acquisition unit" and the "imaging unit" recited in claims.

The reception machine 1 is installed at the reception (entrance) of the medical institution H where medical treatment to the patient P is performed. The reception machine 1 is configured to accept that the patient P has visited the medical institution H for medical treatment, such as, e.g., an examination and a clinical examination. The reception machine 1 is provided with a reception operation unit 11 and a reception machine-side imaging unit 12.

The reception operation unit 11 accepts an input operation for inputting the fact that the patient P has visited the medical institution H by the patient P who has visited the medical institution H. The reception machine 1 acquires a patient number B for the patient P based on the input operation to the reception operation unit 11 by the patient P. The patient number B is identification information for identifying the patient P in the medical institution H.

Note that the reception machine 1 may be configured to accept the fact that the patient P has visited the hospital (to acquire the patient number B) by reading a consultation ticket configured by an IC (integrated circuit) card, a magnetic card, or the like, by using a card reader or the like, instead of inputting to the reception operation unit 11.

The reception machine-side imaging unit 12 captures a face image of the patient P using the reception machine 1. The face image of the patient P captured by the reception machine-side imaging unit 12 is stored in a reference database 41, which will be described later, as a patient reference face image A2. The patient reference face image A2 is a face image of the patient P captured before the patient P to whom medical treatment is performed receives medical treatment. The patient reference face image A2 is acquired in advance as bio-information to be referred to when authenticating the patient P. The reception machine-side imaging unit 12 includes, for example, a CMOS (complementary metal oxide semiconductor) image sensor.

As described above, the reception machine 1 acquires the patient number B and the patient reference face image A2 for the patient P. The reception machine 1 similarly acquires the patient numbers Bα, Bβ, Bγ, . . . and the patient reference face images A2α, A2β, A2γ, . . . for a plurality of patients Pα, Pβ, Pγ, . . . , differing from the patient P for a plurality of patients Pα, Pβ, Pγ, . . . .

Figure 2:
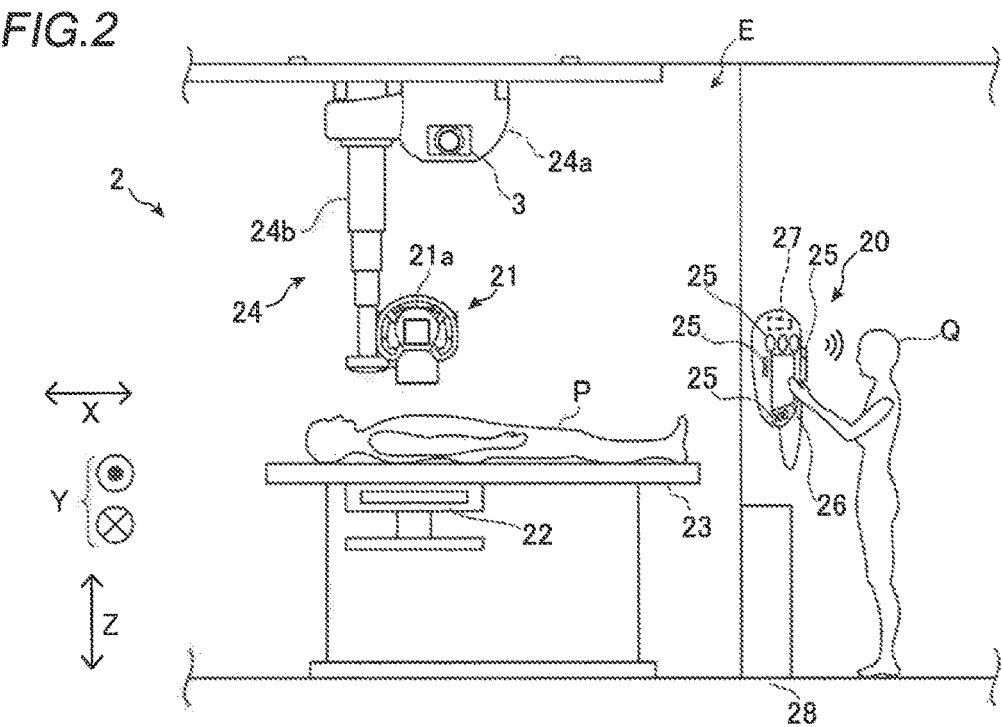
FIG. 2 is a diagram for explaining the configuration of a radiographic imaging device according to the first embodiment.

As shown in FIG. 2, the radiographic imaging device 2 performs radiography on the patient P. The radiographic imaging device 2 is installed in the examination room E where medical treatment to the patient P is performed. The radiographic imaging device 2 includes a console 20, an X-ray irradiation unit 21, an X-ray detection unit 22, a top board 23, a movement unit 24, and a control unit 28. The console 20 includes an operation unit 25, a display 26, and a notification unit 27.

The X-ray irradiation unit 21 includes an X-ray tube 21a for irradiating the patient P with X-rays. The X-ray detection unit 22 is configured to detect the X-rays emitted from the X-ray irradiation unit 21 and passed through the patient P. The X-ray detection unit 22 includes, for example, an FPD (flat panel detector). The patient P to be irradiated with the X-rays is placed on the top board 23.

The movement unit 24 movably holds the X-ray irradiation unit 21. The movement unit 24 includes a horizontal movement unit 24a and a vertical movement unit 24b. The horizontal movement unit 24a is mounted on the ceiling of the examination room E and is configured to movably hold the X-ray irradiation unit 21 in the horizontal direction (X-direction and Y-direction in FIG. 2) via the vertical movement unit 24b (support member). The vertical movement unit 24b movably holds the X-ray irradiation unit 21 in the vertical direction (the Z-direction in FIG. 2).

The operation unit 25 is configured to accept the operation for controlling the radiographic imaging device 2 by the examination operator Q. For example, the operation unit 25 accepts a selection operation for selecting an examination order C, which is information about the medical treatment to be performed on the patient P. The operation unit 25 accepts a selection operation for selecting the irradiation dose and the irradiation position of the X-rays to be emitted to the patient P. The examination operator Q includes a doctor, a radiologist, or the like who uses the radiographic imaging device 2 to perform radiography on the patient P.

Figure 3:
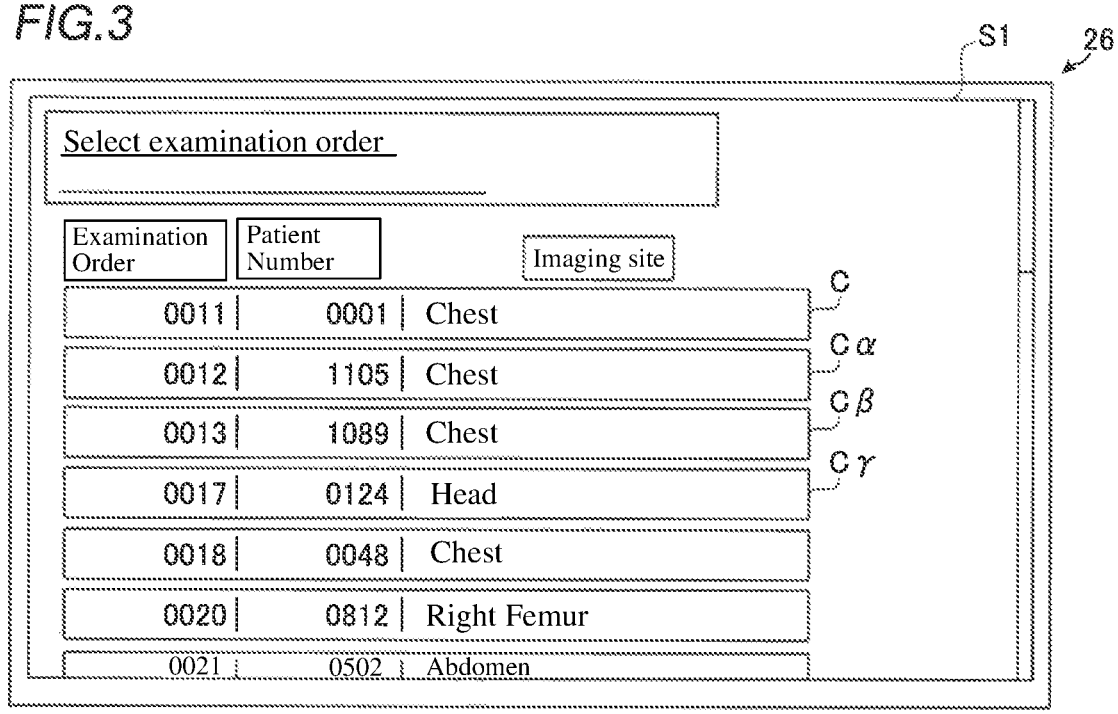
FIG. 3 is a diagram for explaining an examination order selection screen according to the first embodiment.

The display 26 displays information about the operation of the radiographic imaging device 2. The display 26 displays the information about the examination order C, which is information about the medical treatment to be performed on the patient P. The examination order C includes, for example, information for performing a clinical examination on the patient P. The examination order C includes, for example, the information about the imaging site to be imaged at the time of performing radiography on the patient P. Further, as shown in FIG. 3, the display 26 displays an examination order selection screen S1 selectively showing patient identification information B1 (B1α, B1β, B1γ, . . . ) for identifying a plurality of patients P (Pα, Pβ, Pγ, . . . ) and a plurality of examination orders C (Cα, Cβ, Cγ, . . . ) for a plurality of patients P (Pα, Pβ, Pγ, . . . ). The display 26 displays information about the authentication result R (see FIG. 6 and FIG. 7), which is an authentication result of the patient P. The display 26 includes, for example, a liquid crystal display.

The notification unit 27 provides audible notification based on the authentication result R which is the authentication result of the patient P. The notification unit 27 is, for example, a loudspeaker.

The control unit 28 includes, for example, a CPU (Central Processing Unit), a GPU (Graphics Processing Unit), a ROM (Read Only Memory), and a RAM (Random Access Memory) as hardware configurations. The control unit 28 includes a nonvolatile storage medium, such as, e.g., an HDD (Hard Disk Drive) and an SSD (Solid State Drive).

Figure 4:
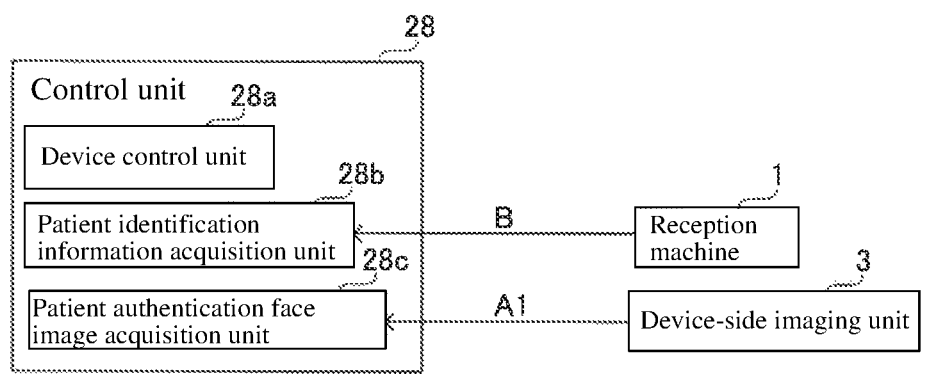
FIG. 4 is a block diagram for explaining the functional configuration of a control unit according to the first embodiment.

As shown in FIG. 4, the control unit 28 includes a device control unit 28a, a patient identification information acquisition unit 28b, and a patient authentication face image acquisition unit 28c as functional components. That is, by executing programs, the control unit 28 is configured to function as the device control unit 28a, the patient identification information acquisition unit 28b, and the patient authentication face image acquisition unit 28c.

The device control unit 28a controls the radiographic imaging device 2. The device control unit 28a controls the radiographic imaging device 2 based on the authentication result R, which is the authentication result of the patient P by an authentication unit 42, which will be described later. The details of the control of the radiographic imaging device 2 will be described later.

The patient identification information acquisition unit 28b acquires patient identification information B1 for identifying the patient P based on the input operation to the reception machine 1. Specifically, the patient identification information acquisition unit 28b acquires the patient number B for the patient P acquired by the reception machine 1 as patient identification information B1 for the patient P. The patient identification information acquisition unit 28b is configured to acquire the patient identification information B1 for the patient P and the examination order C for the patient P in association with each other. Further, the patient identification information acquisition unit 28b acquires the patient identification information B1α, B1β, B1γ, . . . for a plurality of patients Pα, Pβ, Pγ, . . . and the examination orders Cα, Cβ, Cγ, . . . , which are information about the medical treatment (radiography) to be performed on a plurality of patients Pα, Pβ, Pγ, . . . , in the same manner for the plurality of patients Pα, Pβ, Pγ, . . . , which differ from the patient P.

The patient authentication face image acquisition unit 28c acquires the face image of the patient P captured by the device-side imaging unit 3, which will be described later, as a patient authentication face image A1 which is bio-information for authenticating the patient P.

Figure 5:
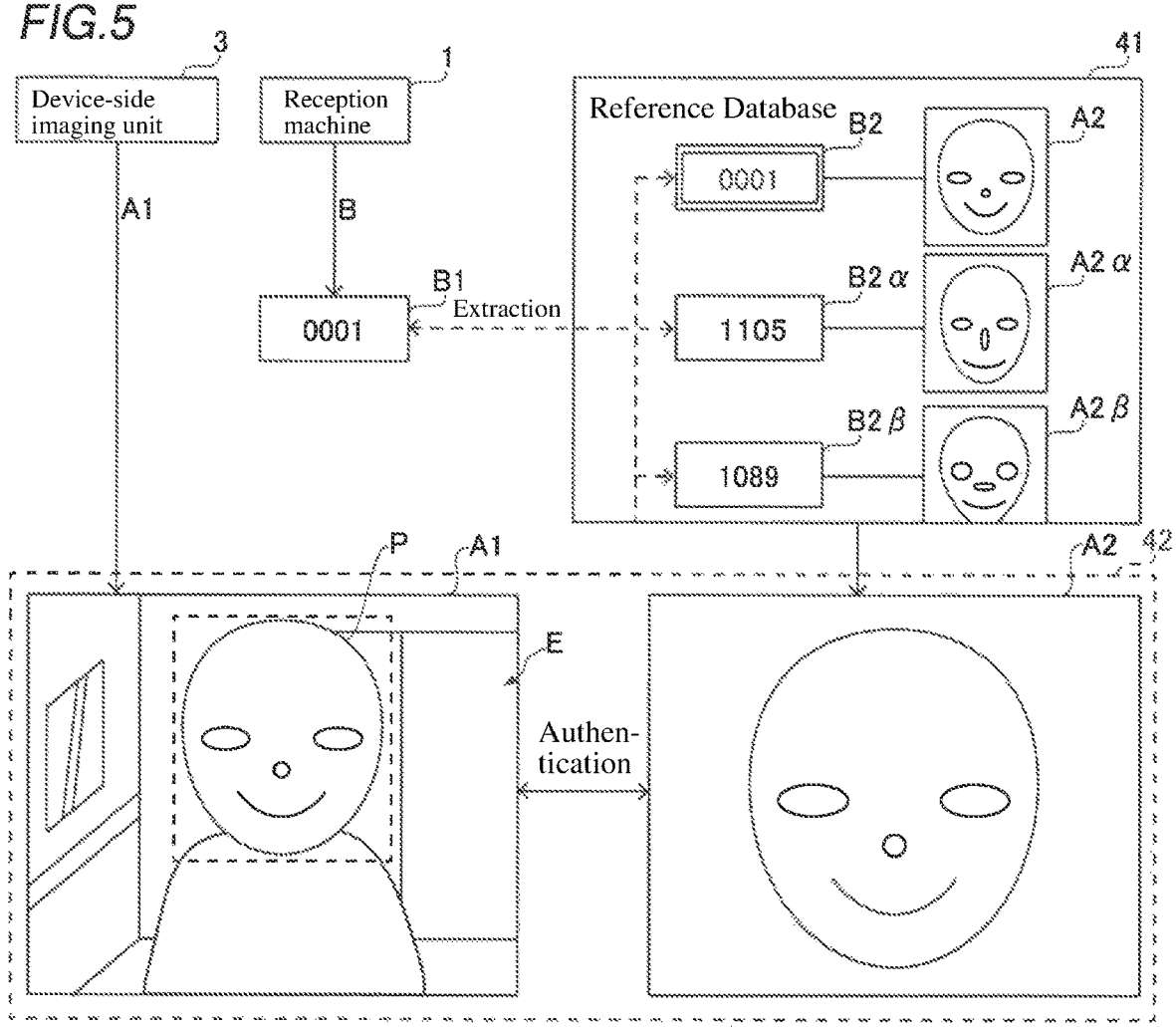
FIG. 5 is a diagram for explaining the authentication of the patient according to the first embodiment.

As shown in FIG. 5, the device-side imaging unit 3 captures the image of the patient P that has entered the examination room E. In this embodiment, the device-side imaging unit 3 is arranged in the examination room E where the radiographic imaging device 2 is installed. Specifically, the device-side imaging unit 3 is mounted on the movement unit 24 of the radiographic imaging device 2 (horizontal movement unit 24a). The device-side imaging unit 3 captures the patient authentication face image A1, which is bio-information for authenticating the patient P. The device-side imaging unit 3 includes, for example, a CMOS image sensor.

The in-hospital server 4 is a server apparatus (information storage apparatus) provided in the medical institution H. The in-hospital server 4 is, for example, a computer. The in-hospital server 4 includes, for example, a CPU, a GPU, a ROM, and a RAM as hardware configurations. The in-hospital server 4 includes a nonvolatile storage medium, such as, e.g., an HDD and an SSD. The in-hospital server 4 is configured to be able to communicate with a plurality of examination devices and computer terminals installed in the medical institution H.

The electronic medical record information and the examination order information on clinical examinations, medical examinations, etc., of a plurality of patients, are centrally managed. The in-hospital server 4 acquires and stores the examination order C for performing the clinical examination on the patient P in association with the patient number B. When the examination order C for radiography is acquired, the patient number B and the examination order C are transmitted to the control unit 28 of the radiographic imaging device 2.

Further, the in-hospital server 4 similarly acquires each of examination orders Cα, Cβ, Cγ, . . . , in association with each of patient numbers Bα, Bβ, Bγ, . . . , also for a plurality of patients Pα, Pβ, Pγ, . . . . The in-hospital server 4 transmits the patient numbers Bα, Bβ, Bγ, . . . and the examination orders Cα, Cβ, Cγ, . . . to the control unit 28 of the radiographic imaging device 2.

The in-hospital server 4 includes, as functional configurations, the reference database 41 and the authentication unit 42. That is, by executing programs, the in-hospital server 4 is configured to function as the reference database 41 and the authentication unit 42.

In this embodiment, the reference database 41 is built in the in-hospital server 4. As shown in FIG. 5, the patient reference face image A2 and the patient reference identification information B2 are stored in association with each other. The patient reference identification information B2 is a patient number B to be referred to when authenticating the patient P.

Specifically, the patient number B for the patient P input based on the input operation to the reception operation unit 11 of the reception machine 1 is stored as patient reference identification information B2 in the reference database 41. The patient reference face image A2 for the patient P captured by the reception machine-side imaging unit 12 of the reception machine 1 is stored in the reference database 41 in association with the patient reference identification information B2 for the patient P. For a plurality of patients Pα, Pβ, Pγ, . . . that differ from the patient P, similarly, each of the patient reference face images A2α, A2β, A2γ, . . . and each of the patient reference identification information B2α, B2β, B2γ, . . . are associated and stored in the reference database 41.

That is, in the reference database 41, the patient reference face images A2 (A2α, A2β, A3γ, . . . ) and the patient reference identification information B2 (B2α, B2β, B3β, . . . ) are stored in association with each other for a plurality of patients P (Pα, Pβ, Pγ, . . . ).

(Patient Authentication)

When a clinical examination for the patient P is performed, the examination order C for the patient P is selected from the examination order selection screen S1 (see FIG. 3) displayed on the display 26. As shown in FIG. 5, the authentication unit 42 authenticates the patient P who has entered the examination room E. In this embodiment, the authentication unit 42 authenticates the patient P based on the reference database 41 in which the patient reference face image A2 and the patient reference identification information B2 are stored in association with each other, the patient identification information B1, and the patient authentication face image A1.

Specifically, the authentication unit 42 extracts the patient reference identification information B2 corresponding to the patient identification information B1 acquired by the patient identification information acquisition unit 28b from the patient reference identification information B2 stored in the reference database 41. The authentication unit 42 is configured to authenticate the patient P based on the patient reference face image A2 stored in the reference database 41 in association with the extracted patient reference identification information B2 and the patient authentication face image A1 captured by the device-side imaging unit 3.

When authenticating the patient P, the authentication unit 42 extracts the patient reference identification information B2 that matches the patient identification information B1 for the patient P from the plurality of patient reference identification information B2 stored in the reference database 41, as shown in FIG. 5. Then, the authentication unit 42 acquires the patient reference face image A2 stored in association with the extracted patient reference identification information B2. Then, by measuring the degree of coincidence between the acquired patient reference face image A2 and the patient authentication face image A1 for the patient P captured by the device-side imaging unit 3, the facial recognition for the patient P is performed.

For the patient authentication face image A1 captured by the device-side imaging unit 3, the authentication unit 42 detects the facial part of the patient P from the patient authentication face image A1. Then, the authentication unit 42 acquires the feature quantity for the detected facial part of the patient P. For the patient reference face image A2, the feature quantity for the facial part is acquired in the same manner. Then, authentication is performed based on the degree of coincidence of the acquired feature quantities.

Further, the authentication unit 42 acquires the authentication result R as an authentication result. When the authentication is successful as the authentication result to the patient P, the authentication unit 42 transmits the authentication result R indicating success to the control unit 28. When the authentication fails as an authentication result to the patient P, the authentication unit 42 transmits the authentication result R indicating failure to the control unit 28.

(Control Based on Authentication Result)

The device control unit 28a controls the switching of the operation of the radiographic imaging device 2 and the notification of the authentication result R, based on the authentication result R.

Figure 6:
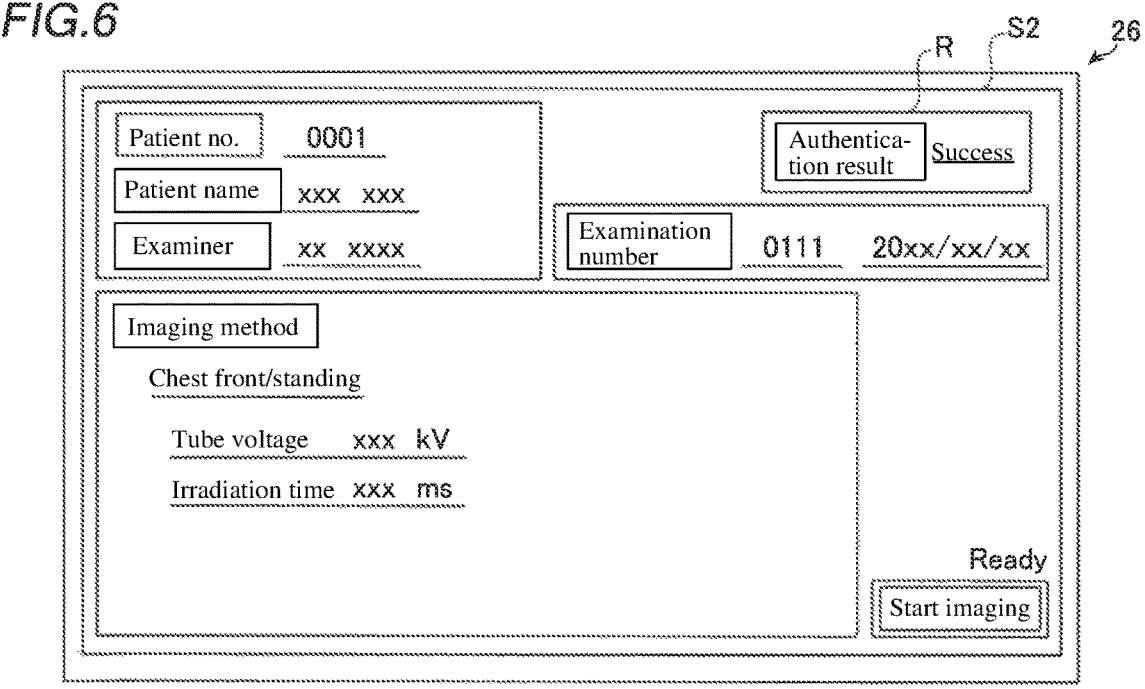
FIG. 6 is a diagram for explaining an imaging screen according to the first embodiment.

As shown in FIG. 6, when the device control unit 28a acquires the authentication result R indicating authentication success, it controls the display 26 to display the imaging screen S2 for radiography based on the patient identification information B1. The imaging screen S2 is a display for starting radiography to the patient P based on the examination order C for the patient P. The imaging screen S2 is a screen display showing the body site of the patient P where radiography is performed, the imaging method, and the like, based on the examination order C. The device control unit 28a displays the information about the authentication result R indicating authentication success in accordance with the display 26.

Further, the device control unit 28a is configured to perform control for switching to the operation preparation mode for performing radiography when the authentication result R indicating authentication success is acquired. In the operation preparation mode, the device control unit 28a causes the X-ray tube 21a and the X-ray detection unit 22 to be ready to perform radiography. Specifically, the device control unit 28a performs control of causing the X-ray tube 21a to be in a state in which X-rays can be emitted and causing the X-ray detection unit 22 to be in a state in which X-rays can be detected.

Figure 7:
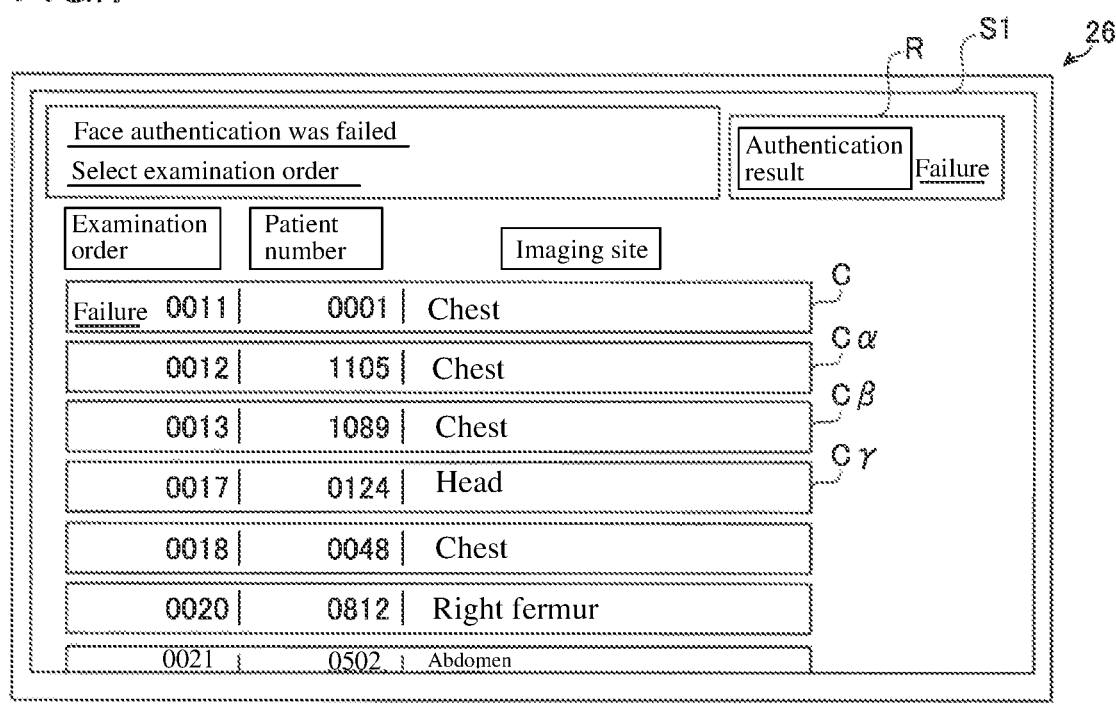
FIG. 7 is a diagram for explaining the display when the authentication result indicating authenticate failure is acquired according to the first embodiment.

Further, as shown in FIG. 7, when the device control unit 28a acquires the authentication result R indicating authentication failure, the device control unit 28a is configured to perform control for causing the display 26 to selectably display the patient identification information B1 (B1α, B1β, B1γ, . . . ) for a plurality of patients P (Pα, Pβ, Pγ, . . . ) and the examination orders C (Cα, Cβ, Cγ, . . . ), which is information about medical treatments (radiography) to be performed on a plurality of patients P (Pα, Pβ, Pγ, . . . ). Specifically, when the authentication result R indicating authentication failure is acquired, the device control unit 28a performs control of displaying the examination order selection screen S1 and the authentication result R indicating authentication failure on the display 26.

Further, the device control unit 28a performs audio notification by the notification unit 27. More specifically, the device control unit 28a performs audio notification by the notification unit 27 so that the authentication success and the authentication failure can be determined based on the authentication result R. Note that authentication success may be notified only when the authentication result R indicating authentication success is acquired. Further note that authentication failure may be notified only when the authentication result R indicating authentication failure is acquired.

Patient Authentication Method by First Embodiment

Figure 8:
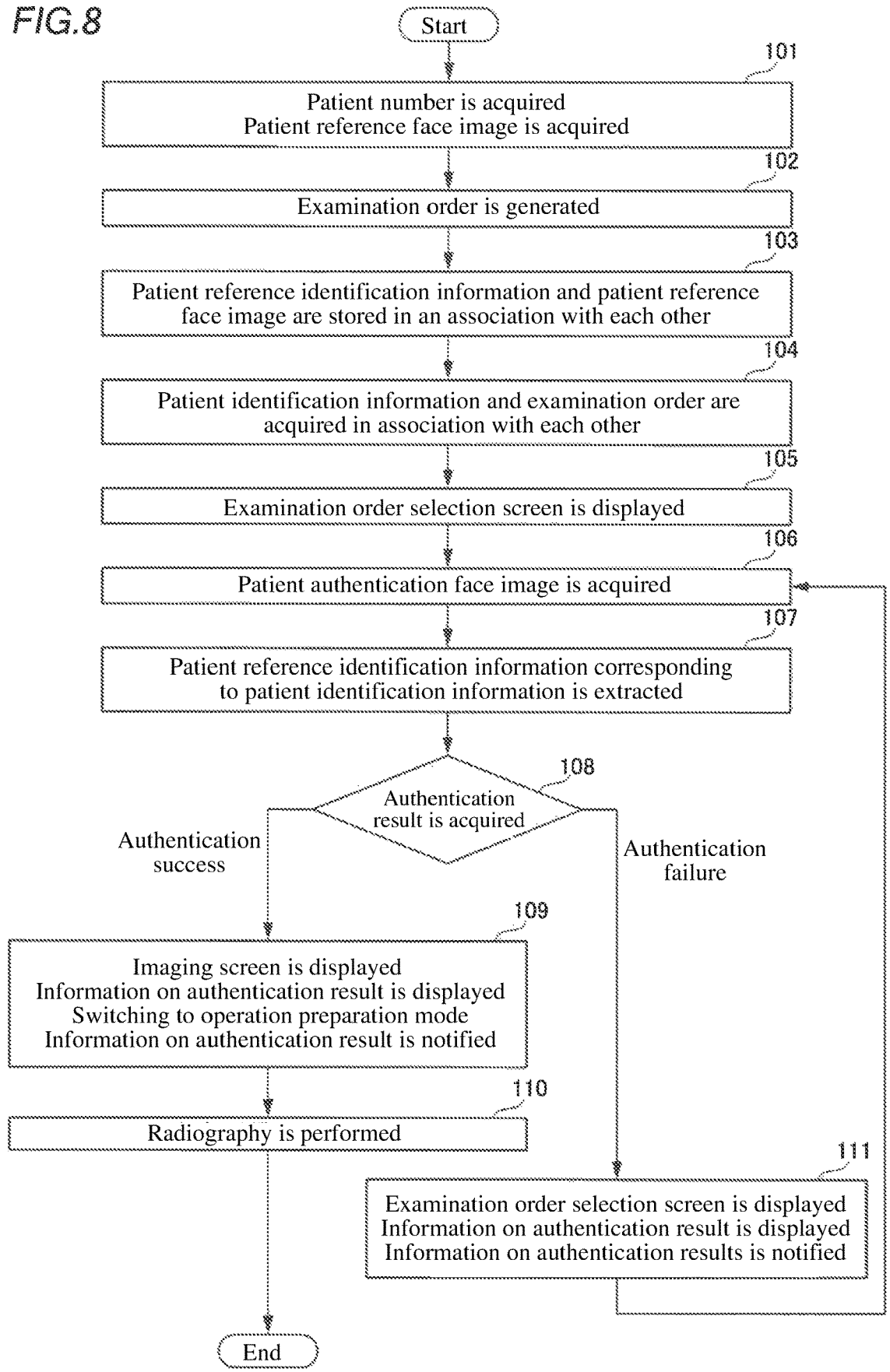
FIG. 8 is a diagram (flowchart) for explaining a patient authentication method according to the first embodiment.

Next, referring to FIG. 8, the patient authentication method using the patient authentication system 100 according to this embodiment will be described.

First, in Step 101, the patient number B for the patient P is acquired by the input operation to the reception machine 1 by the patient P who has visited the medical institution H. The face of the patient P is imaged by the reception machine-side imaging unit 12 provided on the reception machine 1. The face image of the patient P captured by the reception machine-side imaging unit 12 is acquired as a patient reference face image A2.

Next, in Step 102, the examination order C for the patient P is generated based on the patient number B acquired by the reception machine 1. The examination order C is stored in the in-hospital server 4.

Next, in Step 103, the patient number B acquired by the reception machine 1 is stored in the reference database 41 as patient reference identification information B2. Further, the patient reference face image A2 captured by the reception machine-side imaging unit 12 is stored in the reference database 41 in association with the patient reference identification information B2.

Next, in Step 104, the patient number B acquired by the reception machine 1 is acquired as patient identification information B1 by the patient identification information acquisition unit 28b. The examination order C for the patient P is acquired by the patient identification information acquisition unit 28b in association with the patient identification information B1.

Next, in Step 105, the examination order selection screen S1 is displayed on the display 26 so that a plurality of examination orders C (Cα, Cβ, Cγ, . . . ) can be selected.

Next, in Step 106, the patient authentication face image A1 for the patient P who has entered the examination room E to receive the clinical examination based on the selected examination order C is acquired by the device-side imaging unit 3.

Next, in Step 107, among the plurality of patient reference identification information B2 (B2α, B2β, B2γ, . . . ) stored in the reference database 41, the patient reference identification information B2 corresponding to the patient identification information B1 associated with the selected examination order C is extracted.

Next, in Step 108, the degree of coincidence is calculated by performing the image authentication based on the feature quantity of the patient reference face image A2 stored in association with the extracted patient reference identification information B2 and the feature quantity of the patient authentication face image A1 captured by the device-side imaging unit 3. Then, based on the calculated degree of coincidence, when the degree of coincidence is greater than a certain value, an authentication result R indicating authentication success is acquired. When the degree of coincidence is less than the certain value, an authentication result R indicating authentication failure is acquired. When the authentication result R indicating authentication success is acquired, the process proceeds to Step 109. When the authentication result R indicating authentication failure is acquired, the process proceeds to Step 111.

In Step 109, the imaging screen S2 for performing radiography is displayed on the display 26. The information about the authentication result R indicating authentication success is displayed on the display 26. Then, the radiographic imaging device 2 is switched to the operation preparation mode for performing radiography. The information about the authentication result R indicating authentication success is notified by the notification unit 27.

Next, in Step 110, based on the input operation to the operation unit 25 by the examination operator Q, radiography is performed.

On the other hand, in Step 111, the examination order selection screen S1 is displayed on the display 26 so that a plurality of examination orders C (Cα, Cβ, Cγ, . . . ) can be selected. Further, the information about the authentication result R indicating authorization failure is displayed on the display 26. Further, the information about the authentication result R indicating authorization failure is notified by the notification unit 27. When a new examination order C (Cα, Cβ, Cγ, . . . ) is selected, the process returns to Step 106.

It should be noted that either the processing in which the examination order C for the patient P is generated in Step 102 or the processing in which the patient reference face image A2 and the patient reference identification information B2 in Step 103 are stored in the reference database 41 in association with each other may be performed first. Further, either the processing in which the patient reference face image A2 and the patient reference identification information B2 are stored in the reference database 41 in association with each other in Step 103 or the processing in which the examination order C and the patient identification information B1 are acquired in association with each other by the patient identification information acquisition unit 28b in Step 104 may be performed first.

Effects of Patient Authentication System By First Embodiment

In this first embodiment, the following effects can be obtained.

In the patient authentication system 100 of the first embodiment, as described above, the patient P is authenticated based on: the reference database 41 in which the patient reference face image A2 (patient reference bio-information) acquired in advance as bio-information to be referred to when authenticating the patient P and the patient reference identification information B2 to be referred to when authenticating the patient P are stored in association with each other; the patient authentication face image A1 (patient authentication bio-information) acquired by the device-side imaging unit 3 (patient bio-information acquisition unit); and the patient identification information B1 acquired by the patient identification information acquisition unit 28b.

With this, the authentication (confirmation) of the patient P to whom radiography (medical treatment) is performed can be automatically performed without performing the operation of confirming (collating) the patient P based on identification information, such as, e.g., the name and the patient ID of the patient P by the examination operator Q. In this embodiment, the control of the radiographic imaging device 2 (medical device) is performed based on the authentication result R which is the authentication result by the authentication unit 42. With this, the control of the radiographic imaging device 2 can be automatically performed as a preparation for medical treatment such as a clinical examination, based on the authentication result. As a result, it is possible to reduce the workload of the examination operator Q when authenticating the patient P and controlling the radiographic imaging device 2 based on the authentication result R.

Further, in the first embodiment, further effects can be obtained by the following configuration.

That is, in the first embodiment, as described above, it is configured such that the patient reference bio-information (patient reference face image A2) includes the patient reference image (patient reference face image A2) captured in advance by the patient P, the patient bio-information acquisition unit (the device-side imaging unit 3) includes the imaging unit (the device-side imaging unit 3) that captures the patient authentication image (patient authentication face image A1) as patient authentication bio-information (patient authentication face image A1), and the authentication unit 42 authenticates the patient P based on the reference database 41 in which the patient reference face image A2 and the patient reference identification information B2 are stored in association with each other, the patient authentication face image A1 captured by the device-side imaging unit 3, and the patient identification information B1 acquired by the patient identification information acquisition unit 28b.

With this configuration, the patient authentication face image A1 for authenticating the patient P can be easily acquired by imaging the patient P to whom medical treatment is performed by using the radiographic imaging device 2 (medical device) by the device-side imaging unit 3. As the bio-information to be referred to when authenticating the patient P, the patient reference image captured in advance can be used. As a result, the patient P can be automatically authenticated based on the bio-information having characteristics, such as, e.g., a fingerprint, a face, and an iris, which differ depending on individuals. Therefore, when authenticating the patient P to whom medical treatment is performed by using the radiographic imaging device 2, the authentication can be performed with high accuracy.

In the first embodiment, as described above, the patient reference image (patient reference face image A2) includes the patient reference face image A2 in which the face of the patient P is imaged in advance, the imaging unit (device-side imaging unit 3) is configured to capture the patient authentication face image A1 as patient authentication image (patient authentication face image A1), and the authentication unit 42 is configured to authenticate the patient P based on the reference database 41 in which the patient reference face image A2 and the patient reference identification information B2 are stored in association with each other, the patient authentication face image A1 captured by the device-side imaging unit 3, and the patient identification information B1 acquired by the patient identification information acquisition unit 28b.

With this configuration, the image which is a face image of the patient P can be acquired as the patient authentication face image A1 and the patient reference face image A2. As a result, as compared with the case in which a special device for acquiring bio-information is used, the patient authentication face image A1 and the patient reference face image A2 can be more easily acquired by using the device-side imaging unit 3 such as a camera for capturing images.

Further, in the first embodiment, as described above, the authentication unit 42 is configured to extract the patient reference identification information B2 corresponding to the patient identification information B1 acquired by the patient identification information acquisition unit 28b from the patient reference identification information B2 stored in the reference database 41 and authenticates the patient P based on the patient reference face image A2 stored in the reference database 41 in association with the extracted patient reference identification information B2 and the patient authentication face image A1 captured by the device-side imaging unit 3 (imaging unit).

With this configuration, it is possible to extract the patient reference identification information B2 that matches the patient identification information B1 for the patient P to whom radiography (medical treatment) is performed by using the radiographic imaging device 2 (medical device) from the plurality of patient reference identification information B2 stored in the reference database 41. The patient P can be authenticated based on the patient reference face image A2 stored in association with the patient reference identification information B2 matching the patient identification information B1 and the patient authentication face image A1 captured by the device-side imaging unit 3. As a result, as compared with the case in which the patient authentication face image A1 is extracted from the plurality of patient reference face images A2 (A2α, A2β, A2γ, ... ) stored in the reference database 41, the amount of data to be extracted is small, so that the control burden of the authentication unit 42 can be reduced.

In the first embodiment, as described above, the patient identification information acquisition unit 28b is configured to acquire the patient identification information B1 and the examination order C which is information about the medical treatment to be performed on the patient P in association with each other. With this configuration, the patient P shown in the patient identification information B1 and the examination order C which is the informative about the medical treatment (clinical examination) to be performed on the patient P can be acquired in association with each other. As a result, the patient identification information B1 and the examination order C of the patient P to be examined can be easily referred to when performing the clinical examination.

In the first embodiment, as described above, the patient identification information acquisition unit 28b is configured to acquire the patient identification information B1 based on the input operation to the reception machine 1 installed at the reception of the medical institution H in which medical treatment to the patient P is performed. With this configuration, it is possible to acquire the identification information for identifying the patient P based on the information input at the reception when the patient A has visited at the medical institution H including hospitals and clinics. As a result, the patient P does not need to perform an operation for acquiring the patient identification information B1 separately from the reception, so that the increase in the burden on the patient P can be reduced. The patient identification information B1 can be easily acquired based on the input operation to the reception machine 1.

In the first embodiment, as described above, it is configured such that the acquisition of the patient identification information B1 by the patient identification information acquisition unit 28b and the storage of the patient reference identification information B2 in the reference database 41 can be performed based on the input operation to the reception machine 1. With this configuration, the patient identification information B1 and the patient reference identification information B2 are generated based on the common data input when the patient P performs the reception. As a result, since the patient identification information B1 and the patient reference identification information B2 can be generated by one input operation, it is possible to further suppress the increase in the burden on the patient P.

In the first embodiment, as described above, the patient bio-information acquisition unit (device-side imaging unit 3) includes the imaging unit (device-side imaging unit 3) for imaging the patient authentication image (patient authentication face image A1) as patient authentication bio-information (patient authentication face image A1), and the device-side imaging unit 3 is arranged in the examination room E in which the radiographic imaging device 2 (medical device) is installed. With this configuration, when the medical treatment is performed on the patient P by using the radiographic imaging device 2, the patient P who has entered the examination room E where the radiographic imaging device 2 is installed can be imaged. As a result, the patient P to whom the medical treatment is performed can be assuredly authenticated as a target.

In the first embodiment, as described above, the medical device (radiographic imaging device 2) includes the radiographic imaging device 2, and the device-side imaging unit 3 (imaging unit) is mounted on the radiographic imaging device 2. With this configuration, the patient authentication face image A1 can be acquired with respect to the patient P to whom radiography is performed by using the radiographic imaging device 2. As a result, it is possible to prevent a patient error when performing radiography.

In the first embodiment, as described above, the medical device (radiographic imaging device 2) includes the radiographic imaging device 2, and the device control unit 28a is configured to perform at least one of control for switching the operation of the radiographic imaging device 2 and control for notifying the authentication result R, based on the authentication result R. With this configuration, the examination operator Q that performs radiography (medical treatment) by using the radiographic imaging device 2 can easily recognize the authentication result of the patient P by the notification of the authentication result R. Further, since the switching of the operation of the radiographic imaging device 2 is automatically performed based on the authentication result, it is possible to reduce the burden that the examination operator Q performs the operation for controlling the operation of the radiographic imaging device 2 based on the authentication result.

Further, in the first embodiment, as described above, the display 26 for displaying the information about the operation of the radiographic imaging device 2 is further provided, and the device control unit 28a is configured to perform control for making the display 26 display the imaging screen S2 for performing radiography based on the patient identification information B1 when the authentication result R indicating authentication success is acquired. With this configuration, when the authentication result for the patient P is the authentication result R indicating authentication success, the imaging screen S2 for automatically performing radiography can be displayed on the display 26. As a result, it is possible to reduce the burden of the operation for switching to the imaging screen S2 by the examination operator Q.

Further, in the first embodiment, as described above, the device control unit 28a is configured to perform the control of switching to the operation preparation mode for performing radiography when the authentication result R indicating authentication success is acquired. With this configuration, when the authentication result for the patient P is the authentication result R indicating authentication success, the radiographic imaging device 2 can be automatically switched to the operation preparation mode for performing radiography. As a result, it is possible to reduce the burden of the examination operator Q for operating for switching to the operation preparation mode for performing radiography.

In the first embodiment, as described above, the display 26 for displaying the information about the operation of the radiographic imaging device 2 is further provided, and the device control unit 28a is configured to perform control of causing the display 26 to selectively display the patient identification information B1 for a plurality of patients P (Pα, Pβ, Pγ, . . . ) and the examination orders C (Cα, Cβ, Cγ, . . . ) which is information about medical treatment to be performed on a plurality of patients P (Pα, Pγ, . . . ), when authentication result R indicating authentication failure is acquired.

With this configuration, when the authentication result for the patient P is the authentication result R indicating authentication failure, it is possible to cause the display 26 to display the information on the examinations for the plurality of patients P (Pα, Pβ, Pγ, . . . ) including the patient identification information B1 for the plurality of patients P (Pα, Pβ, Pγ, . . . ) for automatically performing radiography. That is, the examination orders C (Cα, Cβ, Cγ, . . . ) for a plurality of patients P (Pα, Pβ, Pγ, . . . ) can be automatically displayed on the display 26 in a selectable state. As a result, it is possible to reduce the burden of the operation for displaying a plurality of examination orders C (Cα, Cβ, Cγ, . . . ) in a selectable state in order to re-select the examination orders C by the examination operator Q.

In the first embodiment, as described above, the device control unit 28a is configured to perform control for notifying the authentication result R by at least one of displaying the information about the authentication result R and performing the audio notification based on the authentication result R. With this configuration, it is possible to easily recognize the information about the authentication result R by visually recognizing the display. Further, the information about the authentication result R can be easily recognized by voice notification.

Further, in the first embodiment, as described above, the patient identification information acquisition unit 28b is configured to acquire the patient identification information B1 which is the identification information of the patient P in the medical institution H where medical treatment to the patient P is performed.

With this configuration, the identification information (such as a patient ID and a patient number B) for identifying the patient P issued in each medical institution H (such as a hospital and a clinic) where the patient P receives medical treatment can be acquired as the patient identification information B1. As a result, it is possible to manage the patient identification information B1 in association with the electronic medical record or the like managed for each medical institution H, authenticate the patient P in association with the electronic medical record, and perform the medical treatment (such as clinical examination and radiography). As such, the consultation and the examination for a single patient P can be easily managed because the information about the patient P can be managed centrally in the medical institution H.

In the first embodiment, as described above, the authentication unit 42 is configured to authenticate the patient P based on the reference database 41 provided in the in-hospital server 4 in the medical institution H where the medical treatment for the patient P is performed, the patient authentication bio-information, and the patient identification information B1.

With this configuration, the patient reference identification information B2 and the patient reference face image A2 can be stored in each medical institution H that performs medical treatment (clinical examination). As a result, since the patient reference face image A2 can be captured each time the patient P visits the medical institution H, the patient reference face image A2 can be captured so as to accurately correspond to the change of the face image due to the aging or the hairstyle change. Therefore, even when the face image of the patient P changes due to the aging or the hairstyle change, it is possible to suppress the decrease in the authentication accuracy for the patient P.

Effects of Patient Authentication Method By First Embodiment

In the patient authentication method according to the first embodiment, the following effects can be acquired.

In the patient authentication method of the first embodiment, by configuring as described above, the patient P is authenticated based on the reference database 41 in which the patient reference face image A2 (patient reference bio-information) acquired in advance as bio-information to be referred to when the patient P is authenticated and the patient reference identification information B2 to be referred to when the patient P is authenticated are stored in association with each other, the patient authentication face image A1 (patient authentication bio-information) acquired by the device-side imaging unit 3 (patient bio-information acquisition unit), and the patient identification information B1 acquired by the patient identification information acquisition unit 28b.

With this, the authentication (confirmation) of the patient P to whom radiography (medical treatment) is performed can be automatically performed without performing the operation of confirming (collating) the patient P by the examination operator Q based on the identification information, such as, e.g., the name of the patient P and the patient ID.

In this embodiment, the control of the radiographic imaging device 2 (medical device) is performed based on the authentication result R, which is the authentication result by the authentication unit 42. With this, the control of the radiographic imaging device 2 can be automatically performed as a preparation for performing medical treatment such as a clinical examination based on the authentication result. As a result, it is possible to reduce the workload burden of the examination operator Q when authenticating the patient P and controlling the radiographic imaging device 2 based on the authentication result R.

Second Embodiment

Figure 9:
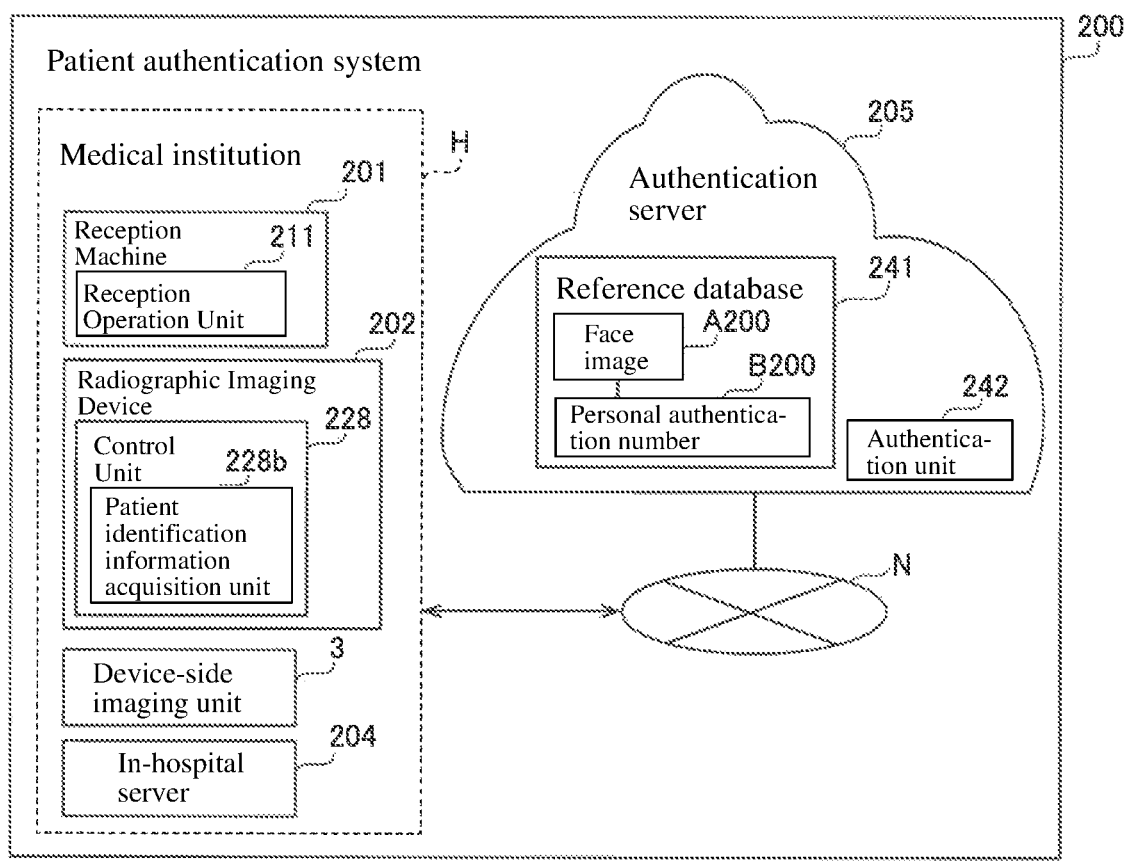
FIG. 9 is a block diagram for explaining the configuration of a patient authentication system according to a second embodiment.

Next, referring to FIG. 9, the configuration of the patient authentication system 200 according to the second embodiment of the present invention is described. In this second embodiment, unlike the first embodiment in which the patient reference face image A2 and the patient reference identification information B2 are stored in the reference database 41 built in the in-hospital server 4, the patient reference face image A2 and the patient reference identification information B2 are stored in a reference database 241 built on a cloud provided separately from the in-hospital server 4. Note that the same configuration as that of the above-described first embodiment is denoted by the same reference numeral in the figures, and the description thereof will be omitted.

As shown in FIG. 9, the patient authentication system 200 according to the second embodiment is provided with a reception machine 201, a radiographic imaging device 202, an in-hospital server 204, and an authentication server 205.

The reception machine 201 is provided with a reception operation unit 211. The reception machine 201 acquires a public personal authentication number B200 for the patient P based on the input operation by the patient P to the reception operation unit 211. The public personal authentication number B200 includes, for example, a personal number (called "My Number") issued by Japan and a social security number issued by the United States. The rest of the configuration of the reception machine 201 is the same as that of the reception machine 1 of the first embodiment.

The radiographic imaging device 202 includes a control unit 228. Its functional configuration includes a patient identification information acquisition unit 228b. That is, by executing a program, the control unit 228 functions as the patient identification information acquisition unit 228b. The hardware configuration of the control unit 228 is the same as the hardware configuration of the control unit 28 of the first embodiment.

The patient identification information acquisition unit 228b acquires patient identification information B1 for identifying the patient P based on the input operation to the reception machine 201. Specifically, the patient identification information acquisition unit 228b acquires the public personal authentication number B200 for the patient P acquired by the reception machine 201 as patient identification information B1 for the patient P. The rest of the function of the patient identification information acquisition unit 228b is similar to that of the patient identification information acquisition unit 28b of the first embodiment.

The in-hospital server 204 retrieves and stores, in the same manner as in the in-hospital server 4 of the first embodiment, the examination order C for performing a clinical examination to the patient P in association with the public personal authentication number B200 for the patient P. When the examination order C for radiography is acquired, it is configured to transmit the public personal authentication number B200 and the examination order C for the patient P to the control unit 228 of the radiographic imaging device 202.

The authentication server 205 includes a reference database 241 and an authentication unit 242. The authentication server 205 is built on a cloud (cloud computing) provided separately from the in-hospital server 204. The authentication server 205 is configured to be able to communicate with the radiographic imaging device 202 via a network N such as the Internet.

The reference database 241 is built on the authentication server 205 (cloud). In the reference database 241, a patient reference face image A2 and patient reference identification information B2 are stored in association with each other in the same manner as in the reference database 41 by the first embodiment (see FIG. 5). The patient reference identification information B2 is a public personal authentication number B200 to be referred to when authenticating the patient P.

Specifically, the public personal authentication number B200 for the patient P issued for each individual managed by the national government, the public organization, and the like is stored as the patient reference identification information B2 in the reference database 241. The public personal authentication number B200 is stored in the authentication server 205 in association with the personal face image A200 corresponding to the public personal authentication number B200. The personal face image A200 corresponding to the public personal authentication number B200 is stored in the reference database 241 as a patient reference face image A2 in association with the patient reference identification information B2.

The authentication unit 242 authenticates the patient P who has entered the examination room E. The authentication unit 242 is configured to authenticate the patient P based on the reference database 241 built on the cloud, the patient authentication face image A1, and the patient identification information B1.

Specifically, the authentication unit 242 extracts the patient reference identification information B2 corresponding to the patient identification information B1 acquired by the patient identification information acquisition unit 228b, from the patient reference identification information B2 stored in the reference database 241. The authentication unit 242 is configured to authenticate the patient P based on the patient reference face image A2 stored in the reference database 241 in association with the extracted patient reference identification information B2 and the patient authentication face image A1 captured by the device-side imaging unit 3. The rest of the configuration of the second embodiment is the same as that of the first embodiment.

Patient Authentication Method By Second Embodiment

Figure 10:
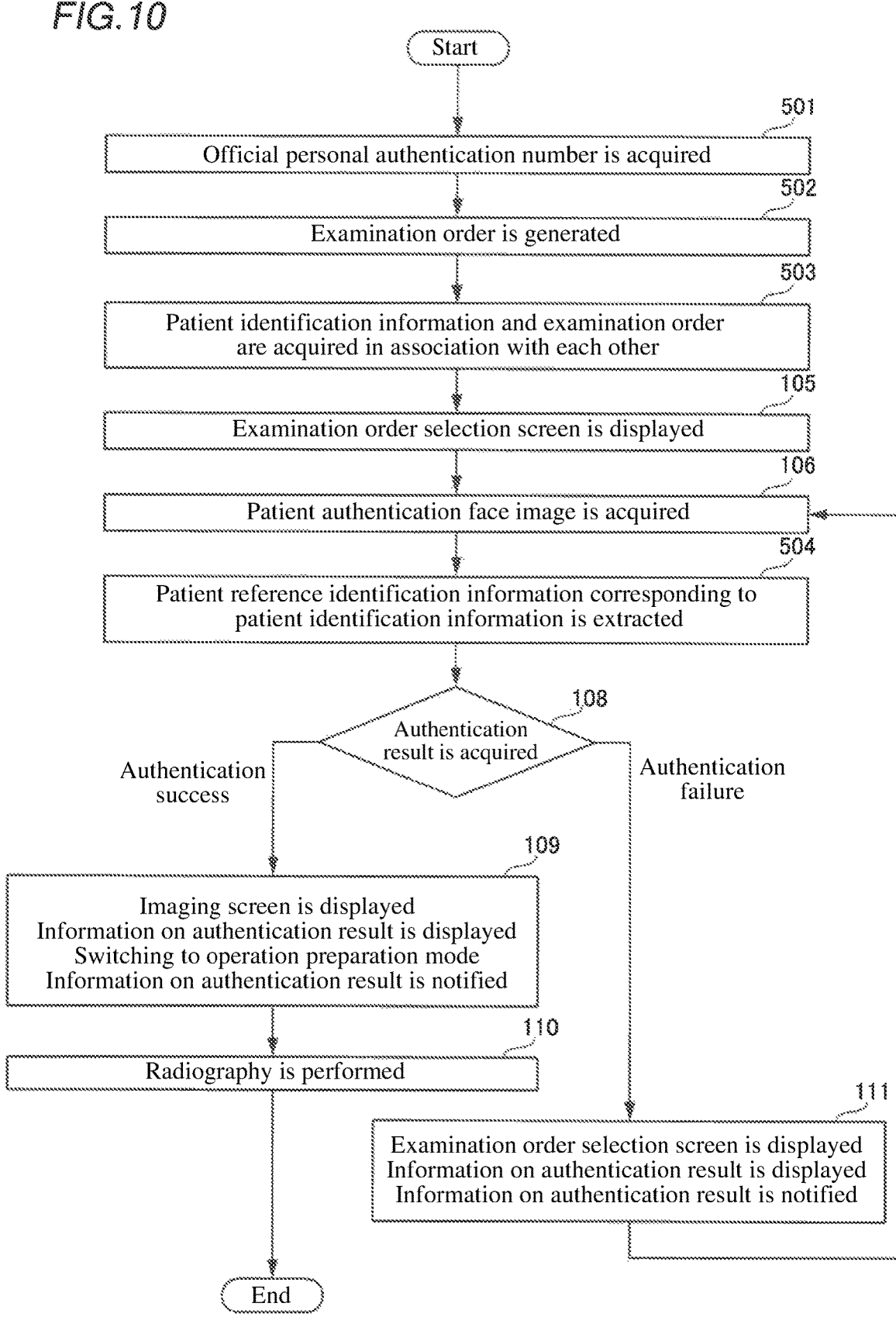
FIG. 10 is a diagram (flowchart) for explaining a patient authentication method according to the second embodiment.

Next, referring to FIG. 10, the patient authentication method using the patient authentication system 200 according to this embodiment will be described. The same method (control processing) as that of the first embodiment is denoted by the same Step number, and the descriptions thereof will be omitted.

First, in Step 501, a public personal authentication number B200 for the patient P is acquired by the input operation to the reception machine 1 by the patient P who has visited the medical institution H.

Next, in Step 502, the examination order C for the patient P is generated based on the public personal authentication number B200 acquired by the reception machine 1. The examination order C is stored in the in-hospital server 204.

Next, in Step 503, the public personal authentication number B200 acquired by the reception machine 1 is acquired by the patient identification information acquisition unit 228b as patient identification information B1. The examination order C for the patient P is also acquired by the patient identification information acquisition unit 228b in association with the patient identification information B1. In Step 105 and Step 106, the same processing as in the first embodiment is performed.

Next, in Step 504, among the plurality of patient reference identification information B2 (B2α, B2β, B2γ, . . . ) stored in the reference database 241, the patient identification information B1 associated with the selected examination order C and the corresponding patient reference identification information B2 are extracted. Thereafter, the same processing as that of the first embodiment is performed in Step 108 to Step 110 and Step 111.

Effects of Second Embodiment

In this second embodiment, the following effects can be obtained.

In the second embodiment, as described above, the patient identification information acquisition unit 228b is configured to acquire the patient identification information B1 which is a public personal authentication number B200. With this configuration, each of the patient individuals can be identified based on the personal authentication number B200 that is publicly managed. As a result, it is unnecessary to generate the patient identification information B1 for identifying the patient P again, so that it is possible to suppress the increase in the burden on the patient P for generating the patient identification information B1.

In the second embodiment, as described above, the authentication unit 242 is configured to authenticate the patient P based on the reference database 241 built on the cloud, the patient authentication face image A1 (patient authentication bio-information), and the patient identification information B1. With this configuration, the patient reference identification information B2 and the patient reference face image A2 can be stored in the reference database 241 built on the cloud without acquiring and storing the patient reference identification information B2 and the patient reference face image A2 in each medical institution H in which the patient P receives medical treatment (clinical examination). As a result, as compared with the case in which the reference database 241 is provided in each medical institution H, the configuration of the system can be simplified.

The other effects of the second embodiment are the same as those of the first embodiment.

Third Embodiment

Next, referring to FIG. 11, the configuration of a patient authentication system 300 according to a third embodiment of the present invention will be described. In this third embodiment, unlike the first embodiment in which the device-side imaging unit 3 is arranged in the examination room E, the device-side imaging unit 303 is arranged outside the examination room E. Note that the same component as that of the first and second embodiments will be denoted by the same reference numeral in the figures, and the descriptions thereof will be omitted.

Figure 11:
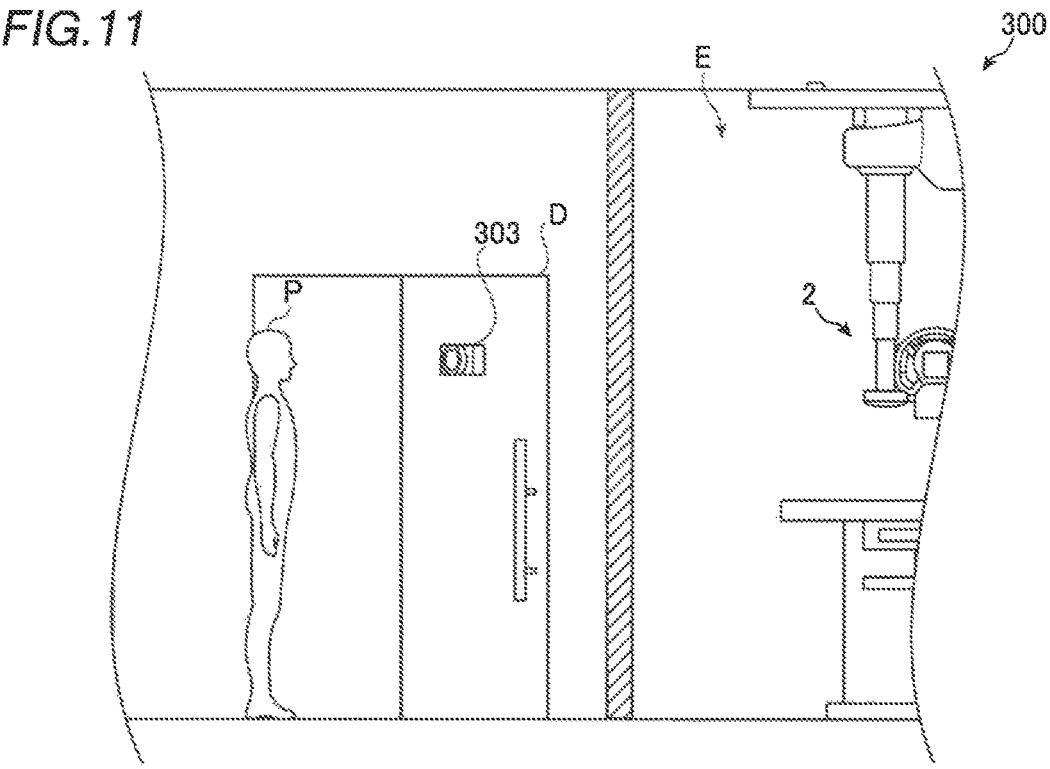
FIG. 11 is a diagram for explaining the configuration of a patient authentication system according to a third embodiment.

The patient authentication system 300 according to the third embodiment is provided with a device-side imaging unit 303, as shown in FIG. 11.

In this embodiment, the device-side imaging unit 303 is arranged to image the patient P entering the examination room E outside the examination room E in which the radiographic imaging device 2 is installed. More specifically, the device-side imaging unit 303 is installed on the outer side of the door D for entering the examination room E so as to capture the face image of the patient P entering the examination room E. The device-side imaging unit 303 acquires a patient authentication face image A1 by capturing the face image of the patient P who is about to enter the examination room E. The rest of the configuration of the third embodiment is the same as that of the first embodiment.

Effects of Third Embodiment

In the third embodiment, the following effects can be acquired.

In the third embodiment, as described above, the patient bio-information acquisition unit (device-side imaging unit 303) includes the imaging unit (device-side imaging unit 303) for capturing the patient authentication image (patient authentication face image A1) as patient authentication bio-information (patient authentication face image A1), and the device-side imaging unit 303 is arranged to image the patient P entering the examination room E outside the examination room E in which the radiographic imaging device 2 (medical device) is installed.

With this configuration, it is possible to capture the image of the patient P who is about to enter the examination room E to receive radiography (medical treatment) by using the radiographic imaging device 2. As a result, the patient P can be imaged before the patient P enters the examination room E, so that the authentication to the patient P can be quickly started. The other effects of the third embodiment are similar to those of the first and second embodiments.

Fourth Embodiment

Next, referring to FIG. 12 and FIG. 13, the configuration of a patient authentication system 400 according to a fourth embodiment of the present invention will be described. In this fourth embodiment, unlike the first embodiment in which the device control unit 28a performs the control of switching to the examination order selection mode when the authentication result R indicating authentication failure is acquired, the device control unit 428a performs the control of switching the radiographic imaging device 402 to an emergency imaging mode in which imaging is performed without selecting the examination order C selected prior to imaging. The same configuration as that of the above-mentioned first to third embodiments are denoted by the same reference numeral in the figures, and the descriptions thereof will be omitted.

Figure 12:
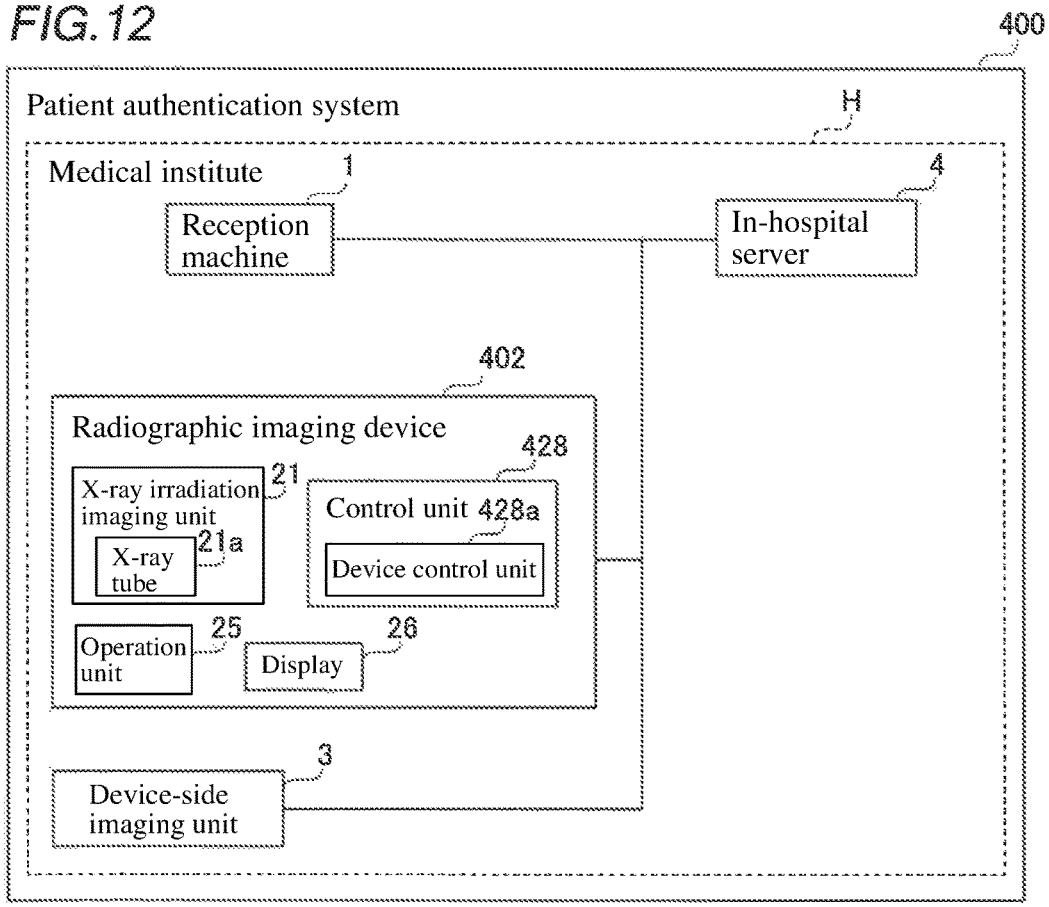
FIG. 12 is a diagram for explaining the configuration of a patient authentication system according to a fourth embodiment.

As shown in FIG. 12, the patient authentication system 400 according to the fourth embodiment is provided with a radiographic imaging device 402. The radiographic imaging device 402 includes a control unit 428. The control unit 428 has a device control unit 428a as a functional configuration. That is, by executing a program, the control unit 428 functions as a device control unit 428a. Note that the rest of the configuration of the control unit 428 is the same as that of the control unit 28 of the first embodiment.

The device control unit 428a controls the radiographic imaging device 402 based on the authentication result R. The control when the authentication result R indicating authentication success is acquired is the same as that of the first embodiment. In this embodiment, the device control unit 428a is configured to perform control for switching to the emergency imaging mode for performing radiography without selecting the examination order C which is the information about medical treatment to be performed on the patient P when the authentication result R indicating authentication failure is acquired. The emergency imaging mode is, for example, a manual imaging mode in which an examination operator Q manually selects and operates the control of the operation (such as the position of the X-ray irradiation unit 21 and the voltage to be applied to the X-ray tube 21a) of the radiographic imaging device 402 for imaging the patient P.

Figure 13:
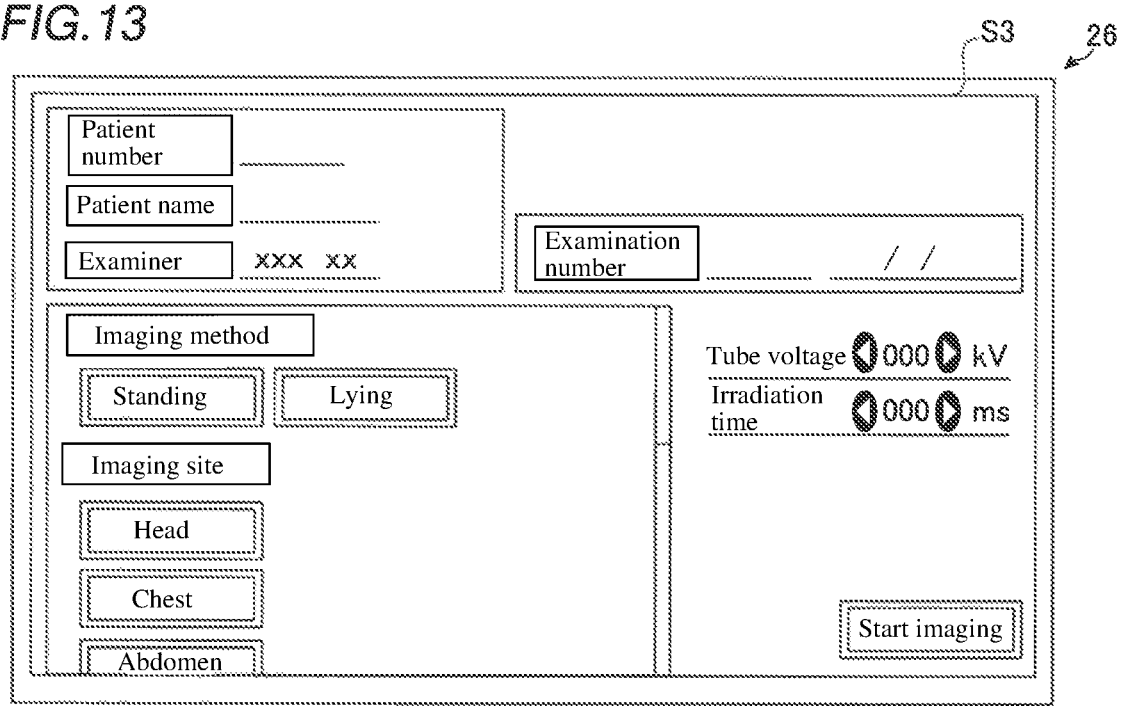
FIG. 13 is a diagram for explaining a display of a display in an emergency imaging mode according to the fourth embodiment.

As shown in FIG. 13, the device control unit 428a displays, on the display 26, an operation screen S3 for determining the operation of the radiographic imaging device 402 by the input operation to the operation unit 25 by the examination operator Q in the emergency imaging mode. The device control unit 428a is configured to perform radiography on the patient P according to the setting determined based on the input operation by the examination operator Q. The rest of the configuration of the fourth embodiment is the same as that of the first embodiment.

Effects of Fourth Embodiment

In this fourth embodiment, the following effects can be obtained.

In the fourth embodiment, as described above, the device control unit 428a is configured to perform control for switching to the emergency imaging mode (manual imaging mode) in which radiography is performed without selecting the examination order C which is the information about medical treatment to be performed on the patient P, when the authentication result R indicating authentication failure is acquired. With this configuration, when the authentication result for the patient P is the authentication result R indicating authentication failure, the radiographic imaging device 402 can be automatically switched to the emergency imaging mode in which radiography is performed without selecting the examination order C which is the information about medical treatment to be performed on the patient P.

Here, in cases where the patient P indicated by the patient identification information B1 included in the selected examination order C differs from the patient who has actually entered the examination room E to receive radiography, there is a case in which the examination operator Q performs radiography on the patient by switching to the emergency imaging mode which is a manual imaging mode for manually operating the radiographic imaging device 402 without selecting the examination order C.

In this embodiment, the device control unit 428a is configured to perform control for switching to the emergency imaging mode in which radiography is performed without selecting the examination order C which is the information about medical treatment to be performed on the patient P, when an authentication result R indicating authentication failure is acquired. Therefore, the radiographic imaging device 402 can be automatically switched to the emergency imaging mode. As a result, it is possible to reduce the burden of the operation for switching to the emergency imaging mode by the examination operator Q. The other effects of the fourth embodiment are similar to those of the first to third embodiments.

Modified Embodiments

It should be understood that the embodiments disclosed here are examples in all respects and are not restrictive. The scope of the present invention is shown by the scope of the claims rather than the descriptions of the embodiments described above and includes all changes (modifications) within the meaning of equivalent and the scope of claims.
(First Modification)

For example, in the first to fourth embodiments described above, an example is shown in which the radiographic imaging device 2 (202, 402) is configured to acquire the information for the patient P (such as, e.g., the examination order C, the patient number B, and the authentication result R) by directly transmitting and receiving information to and from the in-hospital server 4 and the authentication server 205, but the present invention is not limited thereto.

Figure 14:
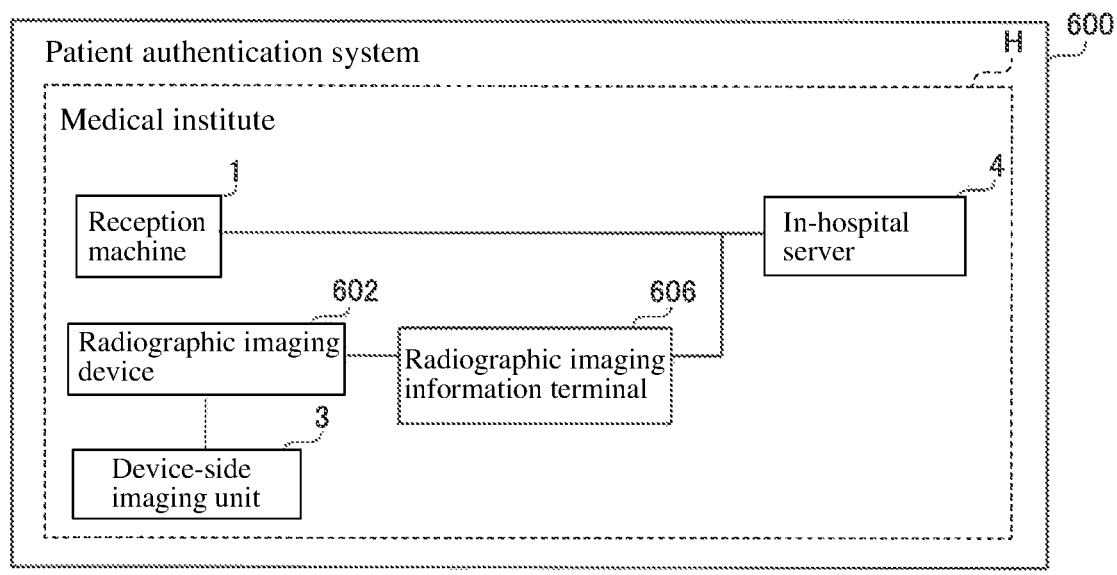
FIG. 14 is a diagram for explaining the configuration of a patient authentication system according to a first modification of the first to fourth embodiments.

For example, as in the patient authentication system 600 according to a first modification shown in FIG. 14, a radiographic imaging information terminal 606 configured to be able to communicate with the in-hospital server 4 may be further provided separately from the radiographic imaging device 602.

Specifically, the radiographic imaging information terminal 606 is configured to be able to communicate with the in-hospital server 4 and acquires the information about patient P (such as, e.g., the examination order C, the patient number B, and the authentication result R) from the in-hospital server 4. The radiographic imaging device 602 may be configured to acquire information about the patient P (e.g., the examination order C, the patient identification information B1, and the authentication result R) from the radiographic imaging information terminal 606. The radiographic imaging information terminal 606 is, for example, a computer terminal.
(Other Modifications)

In the first to fourth embodiments described above, an example is shown in which medical treatment (radiography) is performed on the patient P by using the radiographic imaging device 2 (202 and 402) as an example of the medical device, but the present invention is not limited thereto. For example, medical treatment may be performed on the patient P by using an ultrasonic diagnostic apparatus, an MRI (Magnetic resonance imaging) apparatus of the like. Further, medical treatment may be performed on the patient P by using a PET (positron emission tomography) apparatus, a gamma camera device, or the like.

In the first to fourth embodiments described above, as an example of the radiographic imaging device 2 (202, 402), an example of using a ceiling travel type ordinary X-ray imaging apparatus is shown, but the present invention is not limited thereto. For example, an X-ray fluoroscopic imaging apparatus, an X-ray CT (computed tomography) device, a mammographic device, and the like may be used.

Further, in the first to fourth embodiments described above, an example is shown in which the radiographic imaging device 2 (202 and 402) including the top board 23 on which a patient P is placed is used, but the present invention is not limited thereto. For example, a radiographic imaging device that does not include a top board 23 and performs radiography in the standing posture may be used. Further, a moving type radiographic imaging device may be used in which the top board 23 is not provided and radiographic imaging is performed by arranging the X-ray detection unit 22 to a bed provided separately from the radiographic imaging device 2 (202, 402).

In the first, second, and fourth embodiments, an example is shown in which the device-side imaging unit 3 is mounted on the horizontal movement unit 24*a* of the radiographic imaging device 2, but the present invention is not limited thereto. For example, it may be mounted on the vertical movement unit 24*b* of the radiographic imaging device 2 (202, 402). It may be mounted on the X-ray irradiation unit 21.

Further, in the first, third, and fourth embodiments described above, an example is shown in which the in-hospital server 4 included in the patient authentication system 100 (300, 400) is provided with the authentication unit 42, but the present invention is not limited thereto. For example, the authentication unit 42 may be built in the control unit 28. Also, a terminal (computer) for authentication including the authentication unit 42 may be provided separately.

In the first to fourth embodiments described above, an example is shown in which the operation unit 25, the display 26, and the notification unit 27 are provided in the console 20, but the present invention is not limited thereto. For example, the operation unit 25, the display 26, and the notification unit 27 may be configured separately. Further, the operation unit 25 and the display 26 may be integrally configured by a touch panel or the like.

In the first to fourth embodiments, an example is shown in which the patient reference bio-information (patient reference face image A2) includes the patient reference image (patient reference face image A2) in which the patient P is imaged in advance, the patient bio-information acquisition unit (the device-side imaging unit 3, 303) includes the imaging unit (the device-side imaging unit 3, 303) that captures the patient authentication image (patient authentication facial image A1) as patient authentication bio-information (patient authentication facial image A1), and the authentication unit 42 (242) is configured to authenticate the patient P based on the reference database 41 (241) in which the patient reference face image A2 and the patient reference identification information B2 are stored in association with each other, the patient authentication face image A1 captured by the device-side imaging unit 3 (303), and the patient identification information B1 captured by the patient identification information acquisition unit 28*b* (228*b*), but the present invention is not limited thereto.

For example, the information about the voice (voiceprint) of the patient P may be used as the information patient reference bio-information and the information patient authentication bio-information as bio-information for authenticating the patient P. That is, the patient bio-information acquisition unit may be configured to acquire the voice for the patient P.

In the first to fourth embodiments, an example is shown in which the patient reference image (patient reference face image A2) includes the patient reference face image A2 in which the face of the patient P is imaged in advance, the imaging unit (the device-side imaging unit 3, 303) is configured to capture the patient authentication face image A1 as patient authentication image (patient authentication face image A1), and the authentication unit 42 (242) is configured to authenticate the patient P based on the reference database 41 (241) in which the patient reference face image A2 and the patient reference identification information B2 are stored in association with each other, the patient authentication face image A1 captured by the device-side imaging unit 3 (303), and the patient identification information B1 acquired by the patient identification information acquisition unit 28*b* (228*b*), but the present invention is not limited thereto.

For example, it may be configured to acquire the fingerprint image, the iris image, and the like for the patient P as the patient reference image and the patient authentication image. The imaging unit may be configured to capture a fingerprint image and an iris image of the patient P.

In the first to fourth embodiments described above, an example is shown in which the authentication unit 42 (242) is configured to extract the patient reference identification information B2 corresponding to the patient identification information B1 acquired by patient identification information acquisition unit 28b (228b) from the patient reference identification information B2 stored in the reference database 41 (241) and to authenticate the patient P based on the patient reference face image A2 stored in the reference database 41 (241) in association with the extracted patient reference identification information B2 and the patient authentication face image A1 captured by the imaging unit (device-side imaging unit 3, 303), but the present invention is not limited thereto.

For example, the authentication unit 42 (242) may be configured to authenticate the patient P by extracting the patient reference face image A2 corresponding to the captured patient authentication face image A1 from the reference database 41 (241) by image authentication and acquiring the patient reference identification information B2 associated with the acquired patient reference face image A2.

In the above-mentioned first to fourth embodiments, an example is shown in which the patient identification information acquisition unit 28b (228b) is configured to acquire the patient identification information B1 and the examination order C which is the information about the medical treatment to be performed on the patient P in association with each other, but the present invention is not limited thereto. For example, the patient identification information B1 and the examination order C may be acquired separately. Further, the examination order C may be acquired by the authentication unit 42 (242) instead of the patient identification information acquisition unit 28b (228b).

In the first, third, and fourth embodiments, an example is shown in which the patient identification information acquisition unit 28b (228b) is configured to acquire the patient identification information B1 based on the input operation to the reception machine 1 (201) installed at the reception of the medical institution H in which medical treatment for the patient P is performed, but the present invention is not limited thereto. For example, the patient identification information B1 may be acquired based on the input operation to the terminal used by the acceptor by the acceptor of the medical institution H. Alternatively, the patient identification information B1 may be acquired based on the input of the examination order as a result of the examination by the doctor.

In the first, third, and fourth embodiments, an example is shown in which the acquisition of the patient identification information B1 by the patient identification information acquisition unit 28b and the storage of the patient reference identification information B2 in the reference database 41 are performed based on the input operation to the reception machine 1, but the present invention is not limited thereto. For example, the acquisition of the patient identification information B1 by the patient identification acquisition unit 28b and the storage of the patient reference identification information B2 in the reference database 41 may be performed by input operations to separate terminals.

In the first, second, and fourth embodiments, an example is shown in which the patient bio-information acquisition unit (device-side imaging unit 3) includes the imaging unit (device-side imaging unit 3) for capturing the patient authentication image (patient authentication face image A1) as patient authentication bio-information (patient authentication face image A1) and the device-side imaging unit 3 is arranged in the examination room E in which the medical device (radiographic imaging device 2, 202, 402) is provided, but the present invention is not limited thereto. For example, the device-side imaging unit 3 may be mounted on the ceiling of the outside of the examination room E so that a person who has entered the examination room E can be imaged.

In the first, second, and fourth embodiments, an example is shown in which the medical device (radiographic imaging device 2, 202, 402) includes the radiographic imaging device 2 (202, 402) and the imaging unit (device-side imaging unit 3) is mounted on the radiographic imaging device 2 (202, 402), but the present invention is not limited thereto. For example, the device-side imaging unit 3 may be mounted on the ceiling of the examination room E. Alternatively, it may be mounted on the wall surface of the examination room E. Alternatively, it may be mounted on the X-ray detection unit 22 or the top board 23 on which the patient P is placed.

In the above-described third embodiment, an example is shown in which the patient bio-information acquisition unit (device-side imaging unit 303) includes the imaging unit (device-side imaging unit 303) for capturing the patient authentication image (patient authentication face image A1) as patient authentication bio-information (patient authentication face image A1) and the device-side imaging unit 303 is arranged to image the patient P entering the examination room E outside the examination room E in which the medical device (radiographic imaging device 2) is installed, but the present invention is not limited thereto. For example, the examination operator Q who performs the clinical examination on the patient P may hold (wear) the device-side imaging unit 303.

In the first to fourth embodiments described above, an example is shown in which the medical device (radiographic imaging device 2, 202, 402) includes the radiographic imaging device 2 (202, 402) and the device control unit 28a (428a) is configured to perform control for switching the operation of the radiographic imaging device 2 (202, 402) and control for notifying the authentication result R based on the authentication result R, but the present invention is not limited thereto.

For example, only one of the switching of the operation of the radiographic imaging device 2 (202, 402) and the notification of the authentication result R may be performed. It is also possible to perform the control to switch the operation of the radiographic imaging device 2 (202, 402) only when the authentication result R indicating authentication success is acquired. Similarly, the operation of the radiographic imaging device 2 (202, 402) may be controlled to be switched only when the authentication result R indicating authentication failure is acquired.

In the first to fourth embodiments described above, an example is shown in which the display 26 for displaying the information about the operation of the radiographic imaging device 2 (202, 402) is further provided and the device control unit 28a (428a) is configured to perform control for making the display 26 display the imaging screen S2 for radiography based on the patient identification information B1 when the authentication result R indicating authentication success is acquired, but the present invention is not limited thereto.

For example, the device control unit 28a (428a) may be configured to perform control for making the display 26 display a display prompting the examination operator Q to display the imaging screen S2. The device control unit 28a

(428*a*) may be configured to perform control for making the display 26 display that the authentication result R is successful.

In the first to fourth embodiments described above, an example is shown in which the device control unit 28*a* (428*a*) is configured to perform control to switch to the operation preparation mode for performing radiography when the authentication result R indicating authentication success is acquired, but the present invention is not limited thereto. For example, the device control unit 28*a* (428*a*) may be configured to perform control for making the display 26 display a notification prompting to shift to the operation preparation mode to the examination operator Q.

Further, in the first to third embodiments described above, an example is shown in which the display 26 for displaying the information about the operation of the radiographic imaging device 2 (202) is further provided and the device control unit 28*a* is configured, when the authentication result R indicating authentication failure is acquired, to perform control for making the display 26 selectively display the patient identification information B1 for a plurality of patients P (Pα, Pβ, Pγ, . . . ) and the examination order C (Cα, Cβ, Cγ, . . . ) which is the information about the medical treatment to be performed on a plurality of patients P (Pα, Pβ, Pγ, . . . ), but the present invention is not limited thereto.

For example, when the authentication result R is failure, the examination order C may be newly acquired based on the patient identification information B1 corresponding to the acquired patient reference identification information B2 by acquiring the patient reference face image A2 corresponding to the captured patient authentication face image A1 from the reference database 41 (241) by image authentication and acquiring the patient reference identification information B2 associated with the acquired patient reference face image A2 based on the captured patient authentication face image A1. That is, when the authentication result R indicating authentication failure is acquired, the examination order C for the patient P corresponding to the patient authentication face image A1 in which the authentication is failed may be automatically acquired again.

In the fourth embodiment described above, an example is shown in which the device control unit 428*a* is configured to perform control for switching to the emergency imaging mode in which radiography is performed without selecting the examination order C which is the information about the medical treatment to be performed on the patient P when the authentication result R indicating authentication failure is acquired, but the present invention is not limited thereto. For example, when the authentication is failed, the imaging screen S2 for performing radiography may be displayed based on the newly acquired examination order C by newly acquiring the examination order C for the patient P in which the patient authentication face image A1 is imaged.

Further, in the first to fourth embodiments described above, an example is shown in which the device control unit 28*a* (428*a*) is configured to perform the control of the notification of the authentication result R by at least one of the displaying the information about the authentication result R and performing the audio notification based on the authentication result R, but the present invention is not limited thereto.

For example, the control of the radiographic imaging device 2 (202, 402) to switch to the operation preparation mode may be performed without performing both the displaying the information about the authentication result R and performing the audio notification based on the authentication result R.

In the first to fourth embodiments described above, an example is shown in which the patient identification information acquisition unit 28*b* (228*b*) is configured to acquire the patient identification information B1, which is one of the identification information (patient number B) of the patient P and the public personal authentication number B200 in the medical institution H in which the medical treatment for the patient P is performed, but the present invention is not limited thereto. For example, each time the patient P visits the medical institution H, the number for identifying the patient P may be generated, and the generated number may be acquired as the patient identification information B1. Alternatively, the number of the insurance card possessed by the patient P may be acquired as the patient identification information B1.

In the first to fourth embodiments described above, an example is shown in which the authentication unit 42 (242) is configured to perform one of the authentication of the patient P based on the reference database 241 built on the cloud, the patient authentication bio-information (patient authentication face image A1) and the patient identification information B1, or the authentication of the patient P based on the reference database 41 built on the in-hospital server 4 in the medical institution H where the medical treatment is performed on the patient P, the patient authentication bio-information (patient authentication face image A1), and the patient identification information B1, but the present invention is not limited thereto.

For example, the authentication unit 42 (242) may be configured to authenticate the patient P based on the reference database 41 (241) built in the computer installed in the examination room E, the patient authentication face image A1, and the patient identification information B1. That is, the patient reference face image A2 and the patient reference identification information B2 may be stored in a computer installed in the examination room E. Further, the control unit 28 (device control unit 28*a*, 428*a*) and the authentication unit 42 (242) that controls the medical device (radiographic imaging device 2, 202, 402) may be integrally configured.

In the fourth embodiment described above, an example is shown in which the emergency imaging mode is a manual imaging mode in which the examination operator Q manually selects and controls the operation of the radiographic imaging device 402 for imaging the patient P, but the present invention is not limited thereto. For example, in the emergency imaging mode, the X-ray irradiation unit 21 may be arranged at the position at which the X-rays are emitted by acquiring the position of the X-ray detection unit 22 based on the image captured by the device-side imaging unit 3.

In the emergency imaging mode, for example, by acquiring the size of the patient P based on the image of the patient P captured by the device-side imaging unit 3, the condition for performing the radiography (e.g., the irradiation position of radiation) may be determined based on the size of the patient P.

In the first to fourth embodiments described above, an example is shown in which the device-side imaging unit 3 (303) includes a CMOS image sensor, but the present invention is not limited thereto. For example, the device-side imaging unit 3 (303) may include a CCD (Charge Coupled Device) image sensor. Further, the device-side imaging unit 3 (303) may include a stereo camera.

Aspects

It should be understood by those skilled in the art that the above-described exemplary embodiments are concrete examples of the following aspects.

(Item 1)

A patient authentication system comprising:
- a patient bio-information acquisition unit configured to acquire patient authentication bio-information which is bio-information for authenticating a patient to whom medical treatment is performed by using a medical device;
- a patient identification information acquisition unit configured to acquire patient identification information for identifying the patient;
- an authentication unit configured to authenticate the patient based on a reference database, the patient authentication bio-information acquired by the patient bio-information acquisition unit, and the patient identification information acquired by the patient identification information acquisition unit, the reference database storing patient reference bio-information acquired in advance as bio-information to be referred to when authenticating the patient and the patient reference identification information to be referred to when authenticating the patient in association with each other; and
- a device control unit configured to perform control of the medical device based on an authentication result which is a result of authentication by the authentication unit.

(Item 2)

The patient authentication system as recited in the above-described Item 1,
   wherein the patient reference bio-information includes a patient reference image which is a pre-captured image of the patient,
   wherein the patient bio-information acquisition unit includes an imaging unit for capturing a patient authentication image as the patient authentication bio-information, and
   wherein the authentication unit is configured to authenticate the patient based on the reference database, the patient authentication image captured by the imaging unit, and the patient identification information acquired by the patient identification information acquisition unit, the reference database storing the patient reference image and the patient reference identification information in association with each other.

(Item 3)

The patient authentication system as recited in the above-described Item 2,
   wherein the patient reference image includes a patient reference face image which is a pre-captured face image of the patient,
   wherein the imaging unit is configured to capture a patient authentication face image as the patient authentication image, and
   wherein the authentication unit is configured to authenticate the patient based on the reference database, the patient authentication face image captured by the imaging unit, and the patient identification information acquired by the patient identification information acquisition unit, the reference database storing the patient reference face image and the patient reference identification information in association with each other.

(Item 4)

The patient authentication system as recited in the above-described Item 3,
   wherein the authentication unit is configured to extract the patient reference identification information corresponding to the patient identification information acquired by the patient identification information acquisition unit, from the patient reference identification information stored in the reference database and authenticate the patient based on the patient reference face image stored in the reference database in association with the extracted patient reference identification information and the patient authentication face image captured by the imaging unit.

(Item 5)

The patient authentication system as recited in any one of the above-described Items 1 to 4,
   wherein the patient identification information acquisition unit is configured to acquire the patient identification information and an examination order which is information about medical treatment to be performed on the patient in association with each other.

(Item 6)

The patient authentication system as recited in any one of the above-described Items 1 to 5,
   wherein the patient identification information acquisition unit is configured to acquire the patient identification information based on an input operation to a reception machine installed at a reception of a medical institution in which medical treatment is performed on the patient.

(Item 7)

The patient authentication system as recited in the above-described Item 6,
   wherein acquisition of the patient identification information by the patient identification information acquisition unit and storage of the patient reference identification information in the reference database are performed based on the input operation to the reception machine.

(Item 8)

The patient authentication system as recited in any one of the above-described Items 1 to 7,
   wherein the patient bio-information acquisition unit includes an imaging unit for capturing a patient authentication image as the patient authentication bio-information, and
   wherein the imaging unit is arranged in an examination room in which the medical device is installed.

(Item 9)

The patient authentication system as recited in the above-described Item 8,
   wherein the medical device includes a radiographic imaging device, and
   wherein the imaging unit is mounted on the radiographic imaging device.

(Item 10)

The patient authentication system as recited in any one of the above-described Items 1 to 7,
   wherein the patient bio-information acquisition unit includes an imaging unit for capturing a patient authentication image as the patient authentication bio-information, and
   wherein the imaging unit is arranged outside an examination room in which the medical device is installed to image the patient entering the examination room.

(Item 11)

The patient authentication system as recited in any one of the above-described Items 1 to 10, wherein the medical device includes a radiographic imaging device, and wherein the device control unit is configured to perform at least one of control for switching operation of the radiographic imaging device and control for notifying an authentication result based on the authentication result.

(Item 12)

The patient authentication system as recited in the above-described Item 11, further comprising:

a display configured to display information about the operation of the radiographic imaging device, wherein the device control unit is configured to perform control for displaying an imaging screen for performing radiography based on the patient identification information on the display when the authentication result indicating authentication success is acquired.

(Item 13)

The patient authentication system as recited in the above-described Item 11 or 12, wherein the device control unit is configured to perform control for switching to an operation preparation mode for performing radiography when the authentication result indicating authentication success is acquired.

(Item 14)

The patient authentication system as recited in any one of the above-described Items 11 to 13, further comprising:

a display configured to display information about the operation of the radiographic imaging device, wherein the device control unit is configured to perform, when the authentication result indicating authentication failure is acquired, control for selectively displaying the patient identification information about a plurality of patients and an examination order which is information about medical treatment to be performed on a plurality of patients on the display.

(Item 15)

The patient authentication system as recited any one of the above-described Items 11 to 13, wherein the device control unit is configured to perform control for switching to an emergency imaging mode for performing radiography without selecting an examination order which is information about medical treatment to be performed on the patient, when authentication result indicating authentication failure is acquired.

(Item 16)

The patient authentication system as recited any one of the above-described Items 11 to 15, wherein the device control unit is configured to perform notification control about the authentication result by at least one of a display of information about the authentication result and an audio notification based on the authentication result.

(Item 17)

The patient authentication system as recited in any one of the above-described Items 1 to 16, wherein the patient identification information acquisition unit is configured to acquire the patient identification information which is either identification information of the patient in a medical institution where medical treatment to the patient is performed or a public personal authentication number.

(Item 18)

The patient authentication system as recited any one of the above-described Items 1 to 17, wherein the authentication unit is configured to perform at least one of authentication of the patient based on the reference database built on a cloud, the patient authentication bio-information, and the patient identification information and authentication of the patient based on the reference database built in an in-hospital server in a medical institution where medical treatment to the patient is performed, the patient authentication bio-information, and the patient identification information.

(Item 19)

A patient authentication method comprising:

a step of acquiring patient authentication bio-information which is authentication bio-information of a patient to whom medical treatment is performed by using a medical device;

a step of acquiring patient identification information for identifying the patient;

a step of authenticating the patient based on a reference database in which patient reference bio-information acquired in advance as bio-information to be referred to when performing the authentication of the patient and patient reference identification information to be referred to when performing the authentication of the patient are stored in association with each other, the acquired patient authentication bio-information, and the acquired patient identification information; and a step of controlling the medical device based on an authentication result which is a result of the authentication.

The invention claimed is:

1. A patient authentication system comprising:

a medical device configured to perform an examination on a patient, a reception machine configured to acquire a patient reference identification information, which is identification information for identifying the patient, and a patient reference bio-information, which is biometric information with characteristics that differ from individual to individual;

a server configured to store the patient reference identification information acquired by the reception machine in association with the patient reference bio-information;

a patient bio-information acquisition unit configured to acquire a patient authentication bio-information, which is bio-information with characteristics that differ from individual to individual, about the patient;

wherein the medical device includes a control unit, wherein the control unit is configured to acquire an examination order, which is information about the examination using the medical device, in association with a patient identification information, which is the identification information about the patient, and wherein the server is configured to extract the reference identification information corresponding to the patient identification information associated with the acquired examination order from a plurality of stored patient reference bio-information, and configured to extract the patient reference bio-information stored in association with the patient reference identification information, and wherein the server or the control unit is configured to authenticate the patient based on the patient authentication bio-information acquired by the server and the patient reference bio-information extracted by the server; and wherein a control unit is configured to perform control of the medical device based on an authentication result which is a result of authentication by the server or the control unit.

2. The patient authentication system as recited in claim 1,
wherein the patient reference bio-information includes a patient reference image which is a pre-captured image of the patient,
wherein the patient bio-information acquisition unit includes an imaging unit for capturing a patient authentication image as the patient authentication bio-information, and
wherein the server or the control unit is configured to authenticate the patient based on the patient reference image and the patient reference identification information stored in association with each other by the server, the patient authentication image captured by the imaging unit, and the patient identification information acquired by the control unit.

3. The patient authentication system as recited in claim 2,
wherein the patient reference image includes a patient reference face image which is a pre-captured face image of the patient,
wherein the imaging unit is configured to capture a patient authentication face image as the patient authentication image, and
wherein the server or the control unit is configured to authenticate the patient based on the patient reference face image and the patient reference identification information stored in association with each other by the server, the patient authentication face image captured by the imaging unit, and the patient identification information acquired by the control unit.

4. The patient authentication system as recited in claim 3,
wherein the server is configured to extract the patient reference identification information corresponding to the patient identification information acquired by the control unit, from a plurality of patient reference identification information stored in the server, and
wherein the server or the control unit authenticates the patient based on the patient reference face image stored in the server in association with the patient reference identification information and the patient authentication face image captured by the imaging unit.

5. The patient authentication system as recited in claim 1,
wherein the control unit is configured to acquire the patient identification information based on an input operation to the reception machine installed at a reception of a medical institution in which medical treatment is performed on the patient.

6. The patient authentication system as recited in claim 5,
wherein acquisition of the patient identification information by the control unit and storage of the patient reference identification information in the server are performed based on the input operation to the reception machine.

7. The patient authentication system as recited in claim 1,
wherein the patient bio-information acquisition unit includes an imaging unit for capturing a patient authentication image as the patient authentication bio-information, and
wherein the imaging unit is arranged in an examination room in which the medical device is installed.

8. The patient authentication system as recited in claim 7,
wherein the medical device includes a radiographic imaging device, and
wherein the imaging unit is mounted on the radiographic imaging device.

9. The patient authentication system as recited in claim 1,
wherein the patient bio-information acquisition unit includes an imaging unit for capturing a patient authentication image as the patient authentication bio-information, and
wherein the imaging unit is arranged outside an examination room in which the medical device is installed to image the patient entering the examination room.

10. The patient authentication system as recited in claim 1,
wherein the medical device includes a radiographic imaging device, and
wherein the control unit is configured to perform at least one of control for switching operation of the radiographic imaging device and control for notifying the authentication result based on the authentication result.

11. The patient authentication system as recited in claim 10, further comprising:
a display configured to display information about the operation of the radiographic imaging device,
wherein the control unit is configured to perform control for displaying an imaging screen for performing radiography based on the patient identification information on the display when the authentication result indicating authentication success is acquired.

12. The patient authentication system as recited in claim 10,
wherein the control unit is configured to perform control for switching to an operation preparation mode for performing radiography when the authentication result indicating authentication success is acquired.

13. The patient authentication system as recited in claim 10, further comprising:
a display configured to display information about the operation of the radiographic imaging device,
wherein the control unit is configured to perform, when the authentication result indicating authentication failure is acquired, control for selectively displaying the patient identification information about a plurality of patients and the examination order which is information about medical treatment to be performed on a plurality of patients on the display.

14. The patient authentication system as recited in claim 10,
wherein the control unit is configured to perform control for switching to an emergency imaging mode for performing radiography without selecting the examination order, which is information about medical treatment to be performed on the patient, when an authentication result indicating authentication failure is acquired.

15. The patient authentication system as recited in claim 10,
wherein the control unit is configured to perform notification control about the authentication result by at least one of a display of information about the authentication result and an audio notification based on the authentication result.

16. The patient authentication system as recited in claim 1,
wherein the control unit is configured to acquire the patient identification information which is either identification information of the patient in a medical institution where medical treatment to the patient is performed or a public personal authentication number.

17. The patient authentication system as recited in claim 1,
wherein the server or the control unit is configured to perform at least one of authentication of the patient based on the server built on a cloud, the patient authentication bio-information, and the patient identification information and authentication of the patient based on the server built in an in-hospital server in a medical institution where medical treatment to the patient is performed, the patient authentication bio-information, and the patient identification information.

18. A patient authentication method comprising:
a step of acquiring patient reference identification information, which is identification information for identifying a patient, and patient reference bio-information, which is bio-information having different characteristics depending on an individual, by a reception machine;

a step of acquiring a patient authentication bio-information, which is biometric information with characteristics that differ from individual to individual, by a patient bio-information acquisition unit;

a step of acquiring an examination order, which is information about an examination using a medical device, in association with patient identification information, which is the identification information about the patient, by a control unit of the medical device;

a step of extracting the patient reference bio-information stored in association with the patient reference identification information corresponding to the patient identification information associated with the acquired examination order from a server in which a plurality of patient reference identification information acquired by the reception machine are stored in association with a plurality of patient reference bio-information;

a step of authenticating the patient based on the patient authentication bio-information and the patient reference bio-information; and a step of controlling the medical device based on an authentication result which is a result of the authentication.

* * * * *